US010413195B2

(12) United States Patent
Buschmann et al.

(10) Patent No.: US 10,413,195 B2
(45) Date of Patent: Sep. 17, 2019

(54) METHOD AND DEVICE FOR MONITORING AND IMPROVING ARTERIOGENESIS

(71) Applicants: Ivo Buschmann, Berlin (DE); Axel Pries, Berlin (DE); Ferdinand Lenoble, Berlin (DE)

(72) Inventors: Ivo Buschmann, Berlin (DE); Axel Pries, Berlin (DE); Ferdinand Lenoble, Berlin (DE)

(73) Assignee: Ivo Buschmann, Berlin (DE)

( * ) Notice: Subject to any disclaimer, the term of this patent is extended or adjusted under 35 U.S.C. 154(b) by 680 days.

(21) Appl. No.: 14/810,139

(22) Filed: Jul. 27, 2015

(65) Prior Publication Data
US 2016/0150979 A1 Jun. 2, 2016

Related U.S. Application Data

(63) Continuation of application No. 13/141,575, filed as application No. PCT/EP2009/009263 on Dec. 23, 2009, now abandoned.
(Continued)

(51) Int. Cl.
*A61B 5/02* (2006.01)
*A61B 5/026* (2006.01)
(Continued)

(52) U.S. Cl.
CPC .......... *A61B 5/02007* (2013.01); *A61B 5/026* (2013.01); *A61B 5/0215* (2013.01);
(Continued)

(58) Field of Classification Search
USPC ....... 600/419, 504, 480, 438, 485, 490, 507, 600/505, 506
See application file for complete search history.

(56) References Cited

U.S. PATENT DOCUMENTS

| | | | |
|---|---|---|---|
| 4,602,641 A | * | 7/1986 | Feinberg ............. A61B 5/0263 324/306 |
| 4,712,555 A | | 12/1987 | Thornander et al. |

(Continued)

FOREIGN PATENT DOCUMENTS

| | | |
|---|---|---|
| EP | 1421897 A1 | 5/2004 |
| WO | WO-2010/072416 A1 | 7/2010 |

OTHER PUBLICATIONS

Busch et al., "Arteriogenesis in hypoperfused rat brain," *J Cereb Blood Flow Metab* 23, 621-8, 2003.
(Continued)

*Primary Examiner* — Christian Jang
*Assistant Examiner* — Mitchell E Alter
(74) *Attorney, Agent, or Firm* — Clark & Elbing LLP

(57) ABSTRACT

A method for determining an arteriovascular condition of a subject having an arterial blood flow is shown. The method involves determining a temporal progression of an instantaneous blood flow condition of the arterial blood flow as well as deriving a slew rate of the temporal progression during an increase of the temporal progression. In addition, an arteriovascular condition indicator device is shown, which comprises: an input for receiving an input signal representing an instantaneous arterial blood flow condition of a subject and a slew rate monitor connected to the input. A corresponding control device for providing an activation signal is also shown. The control device comprises a maximum detector connected to the slew rate monitor. A method for stimulation of arteriogenesis is also shown, wherein a temporal progression of an instantaneous blood flow condition is monitored, a slew rate of the temporal progression is derived, and the maximum of the slew rate is determined. An external pressure is applied repeatedly to the arteriovas-
(Continued)

cular section in synchronization with the occurrence of the determined maximum.

8 Claims, 18 Drawing Sheets

Related U.S. Application Data

(60) Provisional application No. 61/140,280, filed on Dec. 23, 2008.

(51) Int. Cl.
    *A61B 5/0215*      (2006.01)
    *A61B 5/022*      (2006.01)
    *A61B 5/0265*      (2006.01)
    *A61B 5/0295*      (2006.01)
    *A61B 5/00*      (2006.01)
    *A61B 8/06*      (2006.01)
    *A61M 1/10*      (2006.01)
    *A61M 1/12*      (2006.01)

(52) U.S. Cl.
    CPC .......... *A61B 5/0261* (2013.01); *A61B 5/0263* (2013.01); *A61B 5/0265* (2013.01); *A61B 5/0295* (2013.01); *A61B 5/02241* (2013.01); *A61B 5/4836* (2013.01); *A61B 8/06* (2013.01); *A61M 1/106* (2013.01); *A61M 1/107* (2013.01); *A61M 1/1067* (2013.01); *A61M 1/1086* (2013.01); *A61M 1/12* (2013.01); *A61M 2205/3334* (2013.01)

(56) References Cited

U.S. PATENT DOCUMENTS

| | | | |
|---|---|---|---|
| RE33,834 E | 3/1992 | Warner et al. | |
| 6,191,111 B1 | 2/2001 | Leschinsky | |
| 7,440,804 B1 | 10/2008 | Min et al. | |
| 2004/0243006 A1* | 12/2004 | Nakata | A61B 5/02007 600/485 |

OTHER PUBLICATIONS

Buschmann, "Direct evidence for therapeutic induction of arteriogenesis in patients with stable angina pectoris via external counterpulsation," European Society of Cardiology Congress, Barcelona, Aug. 29-Sep. 2, 2009.
Buschmann et al., Franz-Volhard-Klinik, Max Delbruck Center, Helios Kli-nikum Buch, Berlin, Germany, "Direct evidence for therapeutic induction of arteriogenesis in patients with stable angina pectoris via external Counterpulsation," *European Heart Journal.* 2009:30 (Suppl);452(2818) (Abstract only).
Buschmann et al., "Improvement of fractional flow reserve and collateral flow by treatment with external counterpulsation (Art. Net.-2 Trial)," *European Journal of Clinical Investigation* 39:866-875, 2009.
Buschmann et al., "Arteriogenesis Versus Angiogenesis: Two Mechanisms of Vessel Growth," *News Physiol Sci* 14, 121-125, 1999.
Buschmann et al., "Therapeutic induction of arteriogenesis in hypoperfused rat brain via granulocyte-macrophage colony stimulating factor," *Circulation* 108, 610-5, 2003.
Dai et al., "Distinct endothelial phenotypes evoked by arterial waveforms derived from atherosclerosis-susceptible and -resistant regions of human vasculature" *Proc Nati Aced Sci USA.* 101(41):14871-6, 2004.

De Smet et al., "Mechanisms of vessel branching: filopodia on endothelial tip cells lead the way," *Arterioscler Thromb Vasc Biol* 29, 639-49, 2009.
Fraisl et al., "Regulation of angiogenesis by oxygen and metabolism," *Dev Cell* 16, 167-79, 2009.
García-Cardeña et al., "Biomechanical activation of vascular endothelium as a determinant of its functional phenotype," *Proc Natl Acad Sci USA* 98, 4478-85, 2001.
Gerhardt et al., "VEGF guides angiogenic sprouting utilizing endothelial tip cell filopodia," *J Cell Biol.* 161(6):1163-77, 2003.
Girard, "Arterial pressure in the chick embryo," *Am J Physiol* 224, 454-60, 1973.
Hellström et al., "Dll4 signalling through Notch1 regulates formation of tip cells during angiogenesis," *Nature.* 445(7129):776-80, 2007.
Jones et al., "Measuring hemodynamic changes during mammalian development." *Am J Physiol Heart Circ Physiol* 287, H1561-9, 2004.
Jones et al., "What determines blood vessel structure? Genetic prespecification vs. hemodynamics," *Physiology (Bethesda)* 21, 388-95, 2006.
Korff et al., "Role of ephrinB2 expression in endothelial cells during arteriogenesis: impact on smooth muscle cell migration and monocyte recruitment," *Blood* 112, 73-81, 2008.
Kudo et al., "Venous identity is lost but arterial identity is not gained during vein graft adaptation," *Arterioscler Thromb Vasc Biol* 27, 1562-71, 2007.
Larrivée et al., "Guidance of vascular development: lessons from the nervous system," *Circ Res* 104, 428-41, 2009.
Lawson et al., "Notch signaling is required for arterial-venous differentiation during embryonic vascular development," *Development* 128, 3675-83, 2001.
Lawson et al., "*sonic hedgehog* and *vascular endothelial growth factor* act upstream of the Notch pathway during arterial endothelial differentiation," *Dev Cell* 3, 127-36, 2002.
Le Noble et al., "Flow regulates arterial-venous differentiation in the chick embryo yolk sac," *Development* 131, 361-75, 2004.
Lindert et al., "OPS imaging of human microcirculation: a short technical report," *J Vasc Res* 39, 368-72, 2002.
Lucitti et al., "Vascular remodeling of the mouse yolk sac requires hemodynamic force," *Development* 134, 3317-26, 2007.
Moyon et al., "Plasticity of endothelial cells during arterial-venous differentiation in the avian embryo," *Development* 128, 3359-70, 2001.
Schaper, "Collateral circulation: past and present," *Basic Res Cardiol* 104, 5-21, 2009.
Styp-Rekowska et al., "An imaging spectroscopy approach for measurement of oxygen saturation and hematocrit during intravital microscopy," *Microcirculation* 14, 207-21, 2007.
Swift et al., "Arterial-venous specification during development," *Circ Res* 104, 576-88, 2009.
Tintu et al., "Hypoxia induces dilated cardiomyopathy in the chick embryo: mechanism, intervention, and long-term consequences," *PLoS One* 4, e5155, 2009.
Van Mierop, "Blood pressure in chick embryos," *UCLA Forum Med Sci* 10, 27- 36, 1970.
Van Mierop et al., "Development of arterial blood pressure in the chick embryo," *Am J Physiol* 212, 43-8, 1967.
Zhong et al., "Gridlock signalling pathway fashions the first embryonic artery," *Nature* 414, 216-20, 2001.
Waetcher et al. "Model-based blood flow quantification from rotational angiography" Med Image Anal. 12(5):586-602 (2008).
International Search Report and Written Opinion for International Application No. PCT/EP2009/009263, dated Mar. 30, 2010 (11 pages).
International Preliminary Report and Written Opinion for International Application No. PCT/EP2009/009263, dated Jun. 29, 2011 (7 pages).

* cited by examiner

FIG. 3A
FIG. 3B
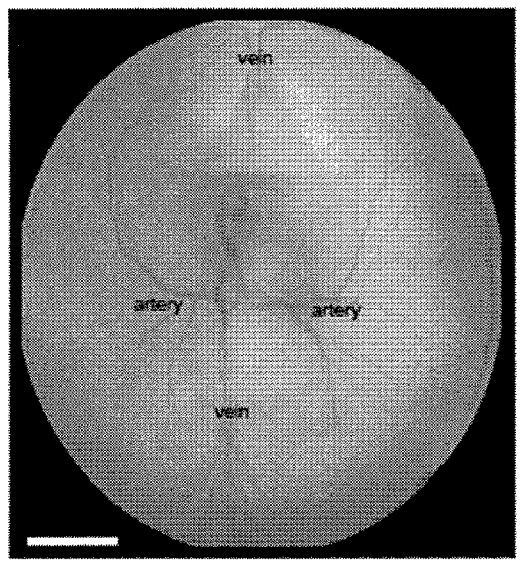
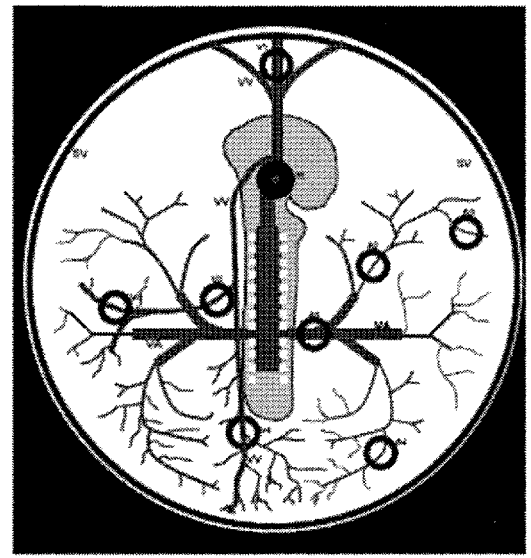

FIG. 3C
FIG. 3D
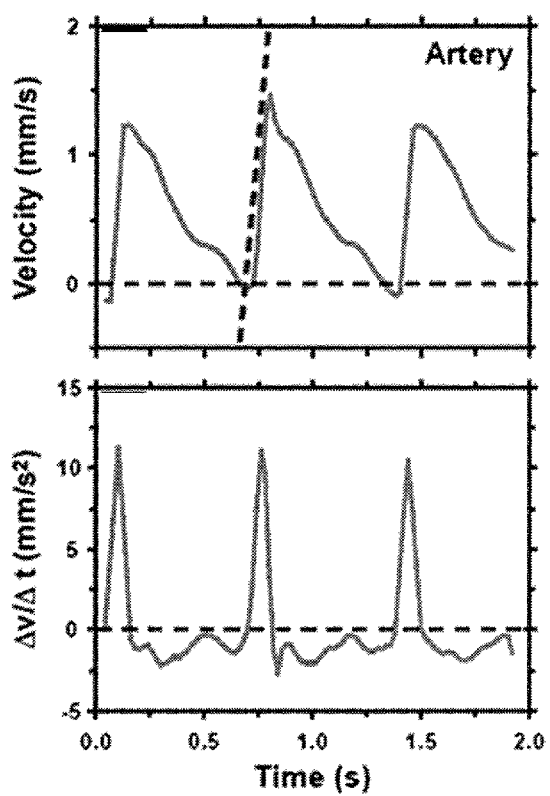
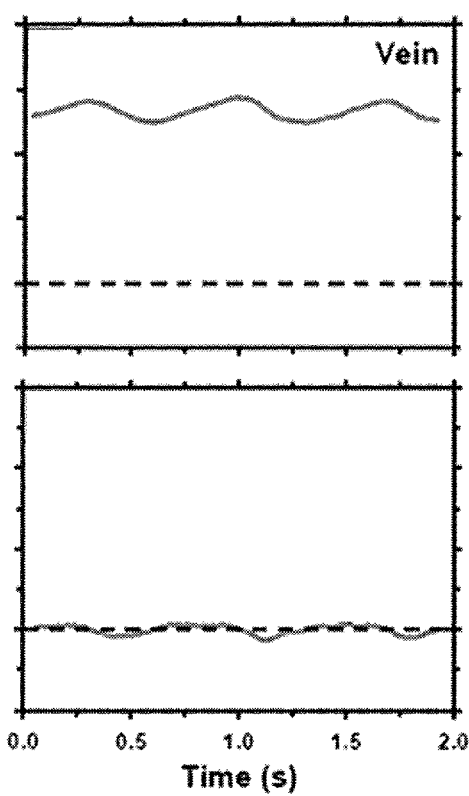
FIG. 3E
FIG. 3F

FIG. 7A
FIG. 7B
FIG. 7D
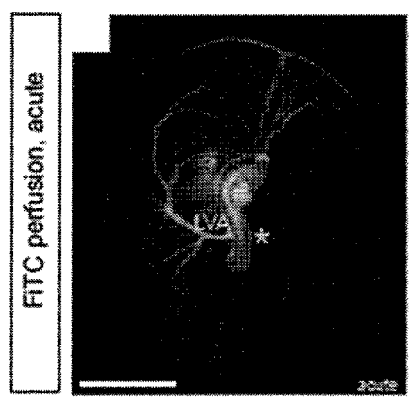
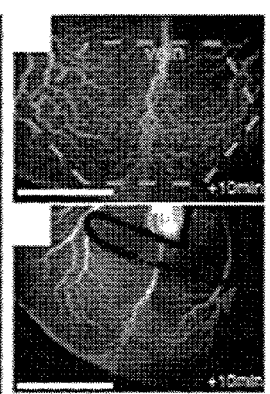
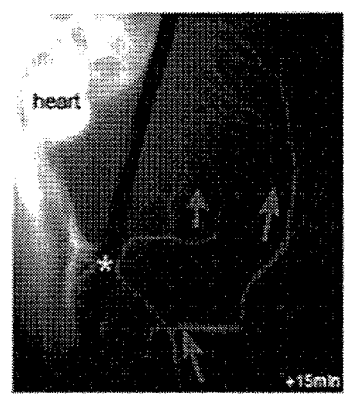
FIG. 7C

Left vitelline artery (LA)

Right vitelline artery (RA)

METHOD AND DEVICE FOR MONITORING AND IMPROVING ARTERIOGENESIS

TECHNICAL FIELD

The present invention relates to devices and methods for sensing the arteriogenic capacity of a patient. The arteriogenic capacity reflects the increase of diameter and/or elastic properties of arterial vessels. In case of pathological properties of particular artery sections, respective treatments are focused on improving these properties by arteriogenesis.

In order to stimulate arteriogenesis improving an arteriovascular condition in an arteriovascular section of a patient prior art approaches are focused on the shear stress of artery vessels generated by the blood flow in the vessel. Studies pertaining to the prior art have suggested to increase the shear stress for training the vessels in pathologic vessel sections for training the vessel section. However, these approaches focused on training the particular vessel section by increasing the shear stress on the vessel have not led to satisfactory results. In other words, stimulating the arteriogenesis by training with high shear stresses has not resulted in reliable training increases. In addition, taking the shear stress as a measure for determining the training performance according to the prior art approaches has not led to a significant and reliable measure for the arteriogenic capacity.

It is therefore an object of the invention, to provide a method and a device for providing an accurate and reliable measure for arteriogenic capacity as well as of the actual status of the arteries. Further, it is an object of the invention to provide a method and a device enabling an effective training of the arteriogenesis of a subject.

SUMMARY OF THE INVENTION

This object is solved by the inventive method for determining an arteriogenic capacity, by the arteriogenic capacity indicator device, the control device as well as the actuator device as defined in the independent claims.

It is the concept underlying the invention to take the variation of the blood flow condition in the artery section as a means for determining the status of the vessel section as well as to take the variation of the blood flow condition actively to increase the arteriogenic capacity by selectively and actively manipulating the variation of the blood flow condition.

The blood flow condition relates to the arterial blood flow, which is inherently linked with the shear stress exerted on the inner vessel surface of the arteriovascular section. In contrast to the prior art which is focused on the blood flow condition itself, i.e. on the shear stress, the invention is focused on the variation, i.e. the temporal progression of an (instantaneous) blood flow condition. As blood flow condition, blood flow velocity, blood flow rate, fluid pressure or shearing force within the arteriovascular section is used as physical quantity. Due to the properties of the vessel, i.e. the properties of the arteriovascular section and the hydrodynamic properties within the arterial vessel, these physical quantities are closely related to each other. According to a preferred model, blood flow velocity, blood flow rate, fluid pressure and shearing force are proportional to each other. The proportionality is given by parameters like blood viscosity, vessel dimensions and relationships among the blood vessel dimensions and the like. In the context of the invention, the term vascular section relates to an arteriovascular section and reflects the inner space delimited by the vessel section as well as the (mechanic) reaction of the vascular section, i.e. elastic and plastic properties of the respective tissue (or vessel) delimiting the arteriovascular section. With regard to the blood flow condition, the term vessel is equivalent to the term vascular section and vice versa. Further, the invention relates to the arterial part of the vascular system of a subject.

According to the invention, an arteriovascular condition in a pathologic section of the arteriovascular system of the subject is determined based on a blood flow condition. A temporal progression a blood flow condition is determined using instantaneous values representing the arterial blood flow. In this respect, the arterial blood flow can be represented by the instantaneous pressure, instantaneous flow velocity, instantaneous flow rate, instantaneous shearing force or by quantities representing these physical quantities. The (arterio-)vascular condition is determined by the slew rate or by another quantity representing the dynamic variations of the temporal progression. The positive variation of the temporal progression, i.e. an increase of the temporal progression is used for deriving the slew rate. The term slew rate relates to a variety of measures and represents any variation of the blood flow condition. According to a preferred embodiment, the slew rate is determined by deriving the progression of the blood flow condition with respect to time. This relates to time continuous as well to time discrete temporal progressions. In a similar embodiment, the slew rate is determined by relating the increase of the progression to the distance of time spanned by the increase. Thus, the slew rate represents the ascending radiant or slope or increase of a straight line between two measure points of the blood flow condition.

In other embodiments, the slew rate represents the maximum frequency or (the power or energy of) maximum frequencies of a representation of the temporal progression in frequency-domain. Since the maximum frequencies represent the maximum slew rate (or the highest slew rates) of the temporal progression, the maximum frequency in the frequency-domain can be used as a measure for the (maximum) slew rate. In particular, the energy or power represented by the area of the progression in the frequency-domain for high frequencies can be used as a measure for the slew rate. The area is enclosed between abscissa and the progression (curve) in frequency-domain for frequencies greater than a minimum frequency at which the progression has a minimum amplitude, the minimum amplitude relating to the highest values of increase in time-domain. The amplitude can be a fixed value or can be related on the complete energy of the progression signal, for example 5% of the total energy of the progression in frequency-domain. In addition, the temporal progression (e.g. as a result of direct or indirect arterial pressure measurements) can be pre-filtered by a low-pass filter or band-pass filter prior to the determination of a measure of the slew rate. Such filters are used to block frequencies not relevant to the determination of the slew rate. The band-pass filter is adapted for passing frequencies, which can be expected for the progression during the systole phase of the arterial blood flow. The low-pass filter is adapted for passing these frequencies occurring during the systole phase and for blocking higher frequencies, e.g. frequencies of noise resulting from the blood flow and the vascular system, in particular resulting from turbulences. Further, a high-pass filter can be used for blocking noise resulting from external impacts onto a sensor measuring the pressure or onto the vascular system.

Further embodiments relate to the shape of the temporal progression by providing a set of predefined (increasing)

curve shapes and respective slew rate values and by matching the determined temporal progression with the curve shape. Any suitable matching or best-fit method can be used to determine the curve shape (of the predefined curve shapes), which shows the highest similarity with the determined (measured) progression. In addition, interpolation between slew rate values can be used to determine a slew rate corresponding to the temporal progression, the determination being based on the predefined curve shapes, similarity measures between predefined curve shapes and the temporal progression, and the respective slew rate values of the curve shapes. The higher the similarity, the higher the impact of the corresponding slew rate values on the resulting slew rate, which is to be determined.

In general, according to the invention, the temporal progression during the systole is relevant to the slew rate, i.e. the invention is based on the observation and determination of the positive slew rates.

Alternatively, it is also possible to determine the slew rates and especially the PSI and RPSI (see below) during the diastole. This embodiment is especially useful in case that an external pressure is applied during the diastole.

The determination of the slew rate is based on measurements of a blood flow condition, the blood flow condition being one of velocity, pressure or shearing force. According to the invention, only one of these physical quantities is measured and provides the values of the temporal progression of the blood flow condition. However, in order to derive the progression from the physical quantities, a predefined function is given, for example a normalizing function or a function deriving one of the physical quantities velocity, pressure or shearing force from a distinct one measured physical quantity. For example, the shearing force can be derived from the blood flow velocity, the blood flow rate, or the fluid pressure according to the predefined function. The predefined function can represent physical relationships among the physical quantities, can represent physical parameters of the fluid path provided by the vascular section, can provide fluid mechanical interrelations or a combination thereof. In a particular preferred embodiment, a measure for providing the blood flow condition is used, which does not depend on the actual diameter of the respective vascular section, i.e. a blood flow condition which does not require measurements of the vessel diameter or other vessel dimensions. Such measures can be provided by determining a value depending on geometric vessel properties and assuming or predefining a constant value which reflects the geometric vessel, i.e. properties of the dimensions of the vascular section and the corresponding fluid dynamic properties, e.g. properties concerning the distribution of pressure or velocity within the cross section of the vascular section. Dependencies on the diameter can be eliminated from the determined value by normalizing a determined value with the predefined diameter (or other vessel dimensions relevant to the flow), i.e. by dividing the determined value by a value equal to or direct proportional to the predefined diameter.

Accordingly, the maximum of the slew rate is one of the maximum slew rate of the blood flow velocity, the blood flow rate, the fluid pressure or the shearing force. Further, the maximum slew rate can be normalized. The normalization basis can be provided by a mean value of the blood flow velocity, of the blood flow rate, of the fluid pressure or of the shearing force (as an average over time). Further, the normalization basis can be provided by a dimension of the blood flow, for example a cross section of the pertaining vascular section. In particular, the normalization basis can be provided by the mean value as described above divided by the cross section diameter of the pertaining vascular section. Further, the normalization basis can be related to a predetermined value, for example by multiplication of one of the above-mentioned normalization basis values with a predetermined value. If the predetermined value is (positive and) smaller than one, the normalization basis is formed by a fraction of the above-mentioned normalization values.

According to a preferred model, changes in velocity, volume flow rate, shear stress and shear rate are mutually proportional since vascular geometry and blood viscosity is given (i.e. is constant). In one embodiment, the maximum slew rate is represented by the peak velocity increase, PVI, which is the (positive) maximum of the slew rate of the blood flow velocity. Preferably, this peak velocity increase is normalized by division by the mean flow velocity, which is the flow velocity averaged over time, preferably averaged over a plurality of pulses. The resulting value is called relative peak velocity increase, RPVI. PVI as well as RPVI both are directly based on the blood flow velocity as underlying physical quantity. However, since the shearing force (in particular the slew rate thereof) is relevant to the arteriovascular condition, a peak shear increase (peak shearing force increase) is derived based on the PVI or RPVI. As interrelationship between velocity-based quantities and shearing force-based quantities, a proportionality factor is given, which is a function of the vessel diameter, the blood viscosity, the radial hematocrit and velocity profile. In a simplified model, vessel diameter, blood viscosity, radial hematocrit profile and velocity profile are combined to one constant value. Due to this proportionality between flow velocity and shear rate or physical stress, values for a relative peak shear increase (RPSI), i.e. the maximum shearing force increase normalized by a mean value of the shearing rate, can be provided identical to respective values of the relative peak velocity increase. In this respect, the term peak is equivalent to maximum as defined above, i.e. the positive peak. The term increase is equivalent to the slew rate as defined above. The relative peak shear increase (=peak shear increase normalized by its mean value) can be further normalized by division by the mean pseudo shear rate, to generate a dimensionless parameter. In particular, this parameter gives a measure, which does not depend on the diameter of the vascular section (or other geometrical properties of the inner tubular room delimited by the vessel. The mean pseudo shear rate is given (according to this simplified model) as $8 \times \bar{v}/d$, wherein $\bar{v}$ is the mean blood velocity (averaged over time), and d is the diameter of the pertaining vessel. The resulting value is dimensionless and is denoted pulse shear index, PSI. Due to the normalization by the vessel diameter, additional measurements or assumptions are necessary for providing the mean pseudo shear rate. Further, the normalization characterizes the pulsatile hemodynamic conditions of a vessel as a single number.

Consequently, in a preferred embodiment of the method for determining an arteriovascular condition of the invention, the RPSI or PSI is determined.

According to the invention, one of these quantities, in particular the RPSI or the PSI, reflecting the temporal progression of the blood flow condition can be used (i) for passively determining an arteriovascular condition and (ii) as a measure for controlling a device actively training the arteriovascular system of a subject. For passively determining the arteriovascular condition, a value representing the maximum slew rate of the temporal progression (or an average thereof) is determined once. Based on this number, the arteriovascular capability is of the subject (in particular of the pertaining part of the vascular system) can be estimated. In addition, a healing process or a training progress can be determined by repeatedly determining the arteriovascular condition, for example in time intervals greater than 3 days, 5 days or 10 days, or greater than 3 days and less than 30 days, preferably between 5 days and 14 days and, in a particular embodiment, about 10 days. Between the values representing the maximum of the slew rate (that is the values representing the measured or derived physical quantities) and the arteriovascular condition (given in form of a grade or an index), a simple relationship is given. This relationship is represented by a monotone increasing relationship or a function such that, for high slew rates, a good or a high arteriovascular condition is given and for low maximum slew rates, a poor, i.e. a low arteriovascular condition is given. According to the repeated measurement results, an arteriogenic capacity can be derived, which is also in monotone relationship with the increase of the arteriovascular condition. That is, if the arteriovascular condition increases significantly in the cause of the repeated measurements, a high arteriogenic capacity of the subject is provided. However, if the arteriovascular condition only shows poor improvement, the arteriogenic capacity of the subject is low. Preferably, the arteriogenic capacity is provided by rates or numbers, for example increasing with improving arteriogenic capacities.

The embodiments for determining the arteriovascular condition and actively training the arteriovascular system described above can be used for monitoring the physical training of athletes or achievement of individuals seeking to improve the physical fitness. In particular, the embodiments relate to non-therapeutic applications and applications for individuals, which do not suffer from cardiovascular diseases. In general, according to one aspect of the invention, the actuation device according to the invention. is used for stimulation of arteriogenesis as described herein.

According to a preferred embodiment, a value for a vascular condition is based on a plurality of measurements or determinations. In particular, plurality of consecutive individual arteriovascular conditions are determined and averaged for providing a resulting (averaged) vascular condition. The consecutive individual arteriovascular conditions can be provided by a number of peak measurements, each peak providing one of the individual arteriovascular conditions. By averaging, random errors can be reduced. According to an embodiment, a measurement time interval is given, for example half an hour, 15 minutes, or 1 minute or less than 30 sec., during which the arterial blood flow is continuously monitored, each peak (each heart beat) providing the basis for deriving a slew rate of the respective temporal progression of the measured quantity. In the course of the measurement time interval, all individual maximum slew rates are given as a total or sum. Instead of a measurement time interval, a predefined number of a heart beats can be given. In this case, the maximum slew rates or the respective values reflecting the arteriovascular conditions of the predefined number of heart beats are averaged.

According to the invention, the measurements are carried out by laser Doppler velocimetry, sonography or magnetic resonance imaging. Other measurements are based on pressure sensing, wrist blood pressure monitoring, finger blood pressure monitoring, sphygmomanometry, plethysmometry, plethysmography, IR-plethysmography, or intravascular blood pressure sensing. The blood pressure can be measured by external pressure of volume variation measurements at the skin region, under which the vascular section is located. In this regard, microphones directly contacting the skin can be used or other instruments monitoring the movement of a medium, the medium being in contact with the vascular system. Even though only relative movements can be used and absolute values of the blood pressure might include a significant error, in general, all measurements suitable for determining the point of time at which the maximum slew rate occurs can be used with the invention. Other suitable measurements are impedance measurements, i.e. measurements of the complex electrical impedance of the vascular section, of the tissue surrounding the vascular section or of the skin (and the underlying tissue), under which the vascular section is located. Such measurements are carried out by applying an AC current (or AC voltage) and measuring the phase and/or frequency distribution of the resulting AC voltage (or current) according to Ohm's law. Further, the myocardial impedance can be measured, in particular for determining the point of time, at which the maximum slew rate occurs. These measurements directly or indirectly measure a physical quantity, from which the blood flow condition is derived, or which forms the basis for determining the blood flow condition based on an other physical quantity. According to a preferred embodiment, laser Doppler velocimetry is used, which includes measurements of phase shifts and/or frequency shifts between received and emitted light and the transformation of the phase shifts into a flow velocity. Thus, the quantity directly measured in this embodiment is a phase or an amplitude of light and the resulting physical quantity is flow velocity. In addition, if the blood flow velocity is measured (as in the embodiment described above), the shearing force can be derived therefrom (by a proportional relationship or by another monotone function).

In a first aspect of the invention, the slew rate is derived as a measure for the arteriovascular condition as described above. According to a second aspect, the time of occurrence of the maximum slew rate is determined for providing the point of time of maximum hydromechanical burden on the pertaining arteriovascular section of the subject. This point of time is critical to active training of the arteriogenic capacity. Thus, the temporal progression of the instantaneous blood flow condition is monitored to determine the point of time of maximum slew rate for activating a supporting mechanism. This supporting mechanism additionally increases the slew rate by appropriate intervention to the pertaining arteriovascular section. This supporting mechanism is provided by an actuator device which exerts pressure onto the arteriovascular section which is to be trained. The actuator device can comprise an apparatus for external pneumatic counterpulsation (ECP) used in the prior art to support the transfer of blood from extremities to the heart for reducing symptoms of ischemia. In contrast to these devices known from the prior art, the actuator device is activated during the systole for additionally increasing the blood pressure resulting in additional maximum slew rates leading to increased arteriogenesis.

The method of the present invention can be performed based on data obtained from any body region where arteries are present. This includes e.g. the base of the tongue.

The present invention provides an arteriovascular condition indicator device for sensing, determining and indicating the point of time of maximum slew rate, a control device for providing a respective activation signal upon detection of the point of time of maximum slew rate as well as an activator device, which can be controlled by the control device. While the indicator device is focused on indicating the value representing the vascular condition, a similar control device is focused on determining the point of time of maximum slew rate in order to appropriately (delayed or undelayed) activate the actuator device. Due to the similar aspects of the control device and the indicator device, most of the components are identical. Further, both devices can be provided as one common apparatus, which selectively provides either an indication of the vascular condition or the point of time of maximum slew rate, or provides both.

An indicator device for indicating an arteriovascular condition comprises an input for receiving an input signal representing the blood flow condition. This input signal is preferably a digital or analogous sensor signal received from a sensor from a measuring device. In addition, the device comprises a slew rate monitor which is connected to the input wherein the slew rate monitor processes the input signal and provides the (actual) slew rate of the blood flow condition represented by the input signal. The slew rate monitor detects the difference between two (consecutive) blood flow conditions and provides the ratio of this difference to the corresponding distance of time passed between the two blood flow conditions. Further, the slew rate monitor can provide a differentiation of the blood flow condition with respect to time by an analog or digital derivation block or circuit. In addition, the slew rate monitor can derive a value representing the slew rate based on a representation of the blood flow condition in the frequency-domain. Further, a maximum detector is provided receiving the output of the slew rate monitor. The maximum detector receives the instantaneous slew rates and provides the (positive) maximum of the slew rates as maximum slew rate. Therefore, the maximum detector has preferably a comparator which allows to compare the slew rates and to identify the maximum slew rate. Further, the maximum detector can have another derivation block, the derivation block receiving the output of the slew rate monitor and provides a differentiation of the slew rate with respect to the time. This corresponds to a second differentiation with respect to time. At the maximum slew rate, the second derivative (=result of the second differentiation) is crossing zero. Thus, the maximum slew rate can be determined by monitoring zero crossings of the second differentiation of the blood flow condition with respect to time whereby the maximum slew rate is defined by the slew rate occurring at the zero crossing of the second derivative.

The maximum slew rate is provided to an output element of the indicator device, the output element outputting a representation of the maximum slew rate as an indicator for the arteriovascular condition. The maximum slew rate can be provided as a displayed nominal value or can be provided by a graphical illustration. In addition, the output element can provide an analog or digital signal having a value which reflects the maximum slew rate.

Depending on the focus and desired function of the device, the output element can output the maximum slew rate together with the time of occurrence. The indicator device further comprises a memory for buffering the maximum slew rate, which is overwritten each time a new slew rate is determined, each time, a higher maximum slew rate is determined or a new average value is provided by an averaging unit of the indicator device, the averaging unit averaging the maximum slew rates.

In another embodiment, a display is adapted or controlled for imaging the (maximum) slew rate or a distribution of (maximum) slew rates at a position of the display, which corresponds to the location of the vascular section or sections corresponding to the slew rate or rates. Preferably, the (maximum) slew rate is determined for a plurality of vascular sections and shown in symbolic manner, e.g. as a color reflecting a slew value or as an arrow reflecting the vector of the blood flow. The magnitude of the vector is the maximum slew rate of the blood flow pressure and the direction of the vector showing the direction of the blood flow. Such imaging can be combined and aligned with a visualization of the spatial progression and location of the respective vascular section. This can be realized by a method comprising the generation of imaging data reflecting the maximum slew rates as described above, by an apparatus comprising a data processing unit adapted for generating these images or this imaging data, as well as by a computer program product, which realizes this method or this apparatus when running on a processing unit. The apparatus can also comprise a visual display for imaging the data. The imaging and the imaging data (which is preferably adapted to be displayed on a monitor) represents a vector field, the position (or origin) of the vectors corresponding to the respective locations of the respective particular vascular sections, the direction of the vectors corresponding to the respective blood flow directions of the respective particular vascular sections and the magnitudes of the vectors representing the slew rate. The magnitude can be represented by the lengths and/or colors of the arrows depicting the vectors. Preferably, the vector field is displayed together with an illustration of the corresponding vascular sections, the illustration being aligned with the vector field.

The output element outputs the maximum slew rate or a value representing the maximum slew rate as an indicator for the arteriovascular condition. The value representing the maximum slew rate can be normalized by a normalizer of the indicator device in order to provide the arteriovascular condition. As normalization factor, a predefined or input value can be used. Further, the normalization factor can be provided by a mean value of the flow condition. Such a mean value can be provided by an external unit or, preferably by the averaging unit which averages successive values representing the maximum slew rate, the maximum slew rates each being related to one peak. Further, as a normalization factor, the ratio of this mean value to a cross sectional diameter can be used. The cross sectional diameter can be provided as an input signal or can be predefined. In addition, the cross sectional diameter can also be represented by the cross sectional area or other values representing dimension of the pertaining vessel. Alternatively, the mean value can be provided by a normalization base input of the indicator device.

According to an aspect of the invention focused on the time of occurrence of the maximum slew rate, a control device is provided. Such a control device provides an activation signal according to the time of occurrence of the maximum slew rate. As described above, a slew rate monitor as well as a maximum detector is provided, similar to the slew rate monitor and the maximum detector as described above. However, if the maximum detector receiving the actual slew rate identifies the occurrence of a maximum for the slew rate, a signal to an activation output of the control device is provided. Thus, the maximum detector is connected to the activation output, wherein the activation output is suited to output an activation signal upon receipt of a signal (of a new maximum slew rate) provided by the maximum detector. Again, for an active training of the arteriovascular condition, it is important to identify the point of time at which the maximum slew rate occurs for coordinating actions on the pertaining arteriovascular section in response to the activation signal. Further, the activation output can be synchronized with the points of time at which the maximum slew rate occurs. The activation signal can be provided with a predefined phase difference to the point of time at which the maximum slew rate occurs. In addition, the activation signal can be delayed to the point of time at which the maximum slew rate occurs by predefined delay. The delay as well as the phase difference can reflect the behavior of an actuator device controlled by the activation signal and can reflect the desired activation time with regard to the point of time at which the maximum slew rate occurs.

According to a further aspect of the invention, an actuator device is provided, which is adapted for being controlled by the activation signal provided by the control device (or by the indicator device, if the indicator device provides a signal of the point of time at which the slew rate occurs). The actuator device comprises both, an actuator surface as well an actuator element adapted to move the actuatable surface. The actuator element is connected to an input of the actuator device at which an activation signal is received. Thus, an activation signal applied to the input of the activator device initiates a movement of the actuatable surface by the actuator element according to the point of time at which the maximum slew rate occurs. Thus, the actuator device is adapted to be actuated at a frequency corresponding to the blood pressure signal of the subject. Since the (positive) maximum of the slew rate is given as indicator for activation, the arteriovascular condition is determined by the slope of the systole. The same applies to the point of time at which the maximum slew rate occurs. The actuator device is triggered by the occurrence of the maximum slew rate. Between trigger and occurrence, a constant phase difference or time difference can be provided. The actuator device is synchronized to the occurrence of the maximum slew rate. The actuator applies an external pressure onto the vascular section in synchronization with the occurrence of the determined maximum. The actuation can be delayed or can be advanced in time. Actuations in advance require synchronization by previous measurements of the time of occurrence of the maximum slew rate. The delay (or the advance in time) can be predetermined or can be a function of the heart beat frequency reflected by the temporal progression, e.g. a monotonically increasing function.

The control device, together with the actuator device performs a method for stimulation of arteriogenesis. Such method for stimulation of arteriogenesis comprises to exert pressure onto the arteriovascular section or tissue to be treated in response to the determination that a maximum slew rate occurs. The pressure can be applied at the point of time at which the maximum slew rate occurs. As an alternative, the application of pressure is initialized a predefined time before the occurrence of the maximum slew rate or a predefined time after occurrence of the maximum slew rate. This corresponds to a phase shift between the detection of the maximum slew rate and the application of pressure. By the application of pressure, the slew rate resulting from the systole is supported by an additional external application of pressure. By the synchronization of occurrence of the maximum slew rate with the activation of the actuator device the additional pulses, resulting from the actuator are aligned to the slew rate measured in the arteriovascular section. This increases the maximum slew rate and therewith increases the training effect, i.e. the enhancement of the arteriogenic capacity. Thus, arteriogenesis is trained by determining the maximum of the slew rate resulting from the systole, activating the actuator device according to the occurrence and therewith increasing the slew rate within the arteriovascular section by external stimulation (=application of pressure). In an alternative embodiment, the slew rate of this systole is determined by sensing electrodes according to an electrocardiogram device. In the same way, the control device identifying a point of time at which the maximum slew rate occurs can comprise an input receiving an input signal representing an instantaneous arterial blood flow condition not at the pertaining arterial vascular section but within the heart. Since the point of time at which the maximum slew rate occurs within the arteriovascular section correlates with the heartbeat, measuring the heartbeat is an alternative if only the time at which the maximum slew rate occurs is necessary. Thus, for synchronization of the actuator device with a point of time at which the maximum slew rate occurs, ECG-electrodes can be used (for example within the inventive control device) for determining the point of time at which the maximum slew rate occurs within the arteriovascular section, i.e. the point of time to which the actuation of the actuator device correlates.

Consequently, the present invention also relates to a method for stimulation of arteriogenesis, comprising: determining a temporal progression of an instantaneous blood flow condition of the arterial blood flow through an arteriovascular section of a subject; deriving a slew rate of the temporal progression during an increase of the temporal progression; and determining the maximum of the slew rate, wherein an external pressure is applied repeatedly to the arteriovascular section in synchronization with the occurrence of the determined maximum.

Preferably, said external pressure is repeatedly applied to the arteriovascular section by an external counterpulsation (ECP) device which is controlled by an arteriovascular condition indicator or control device. ECP is known in the art (see U.S. Pat. No. 6,191,111). A possible arteriovascular condition indicator or control device which can be used according to this aspect of the invention is the arteriovascular condition indicator device or the arteriovascular condition control device as described above.

In a preferred embodiment, the arteriovascular condition indicator or control device is for determining a relative peak shear increase (RPSI) and/or a pulse shear index (PSI) as described above.

The methods and devices of the present invention can be applied both on human and animal patients.

The methods and devices of the present invention can also be applied in order to determine whether the introduction of catheters e.g. in the legs or in the heart region has been successful, because such operations result in changes of arteriovascular conditions which can be determined as disclosed herein.

Studies have been carried out proving the increased arteriogenesis by the inventive training method. In one study, "Direct evidence for therapeutic induction of arteriogenesis in patients with stable angina pectoris via external Counterpulsation" by Eva-Elina Buschmann et. al., Franz-Volhard-Klinik, Max Delbrück Center, Helios Klinikum Buch, Berlin, Germany, 24 Patients (age 51-71) with stable coronary artery disease have been enrolled. One group underwent 35 1-hour sessions of training with the actuator device within 7 weeks. The other group has not been trained and forms the control group. The collateral flow index (CFI) reflecting the collateral circulation has been measured continuously. The CFI of the trained group has increased significantly from $0.09 \pm 0.017$ to $0.14 \pm 0.018$ ($p=0.018$), whereas the control group did not show significant improvements ($p=0.003$). Further, a significant reduction of the CCS classification occurred for the trained group, in contrast to the non-trained group (stable classification). Additionally, the study showed a significant increase of the D/S ratio (peak diastolic amplitude/peak systolic amplitude) from 0.9 (±0.06) to 1.1 (±0.05).

During further clinical studies, it has been demonstrated that the PSI value also correlates with the diameter of the respective arterial blood vessel (see FIG. 10). This could also be confirmed in chicken embryos (FIG. 11). In a patient with shunt operation, however, the RPSI remained constant in view of an increasing diameter due to the increased blood flow in this patient (FIG. 12).

Figure 1:
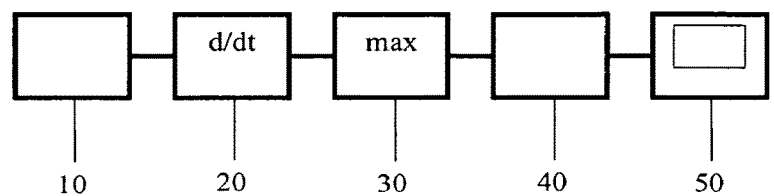
FIG. 1 shows a block diagram of a system suitable for carrying out the invention.

The differentiator 20 provides a derivation of its input with respect to time at an output of the differentiator 20. The system of FIG. 1 comprises a measuring device 10, for example a sensor together with a data acquisition unit, which is connected to a differentiator 20. Thus, the signal output by the measuring device 10 is differentiated with respect to time t. Therefore, the measuring device provides an instantaneous blood flow condition, for example a blood flow velocity. The differentiator 20 forms the slew rate of the temporal progression of the blood flow velocity provided by measuring device 10 as a signal. The slew rate 20 is applied to a maximum detector 30 which identifies and provides the (positive) maximum of the slew rate provided by the differentiator 20. This maximum of the slew rate, preferably together with the time of occurrence of the maximum is provided to a memory 40 which is used as a buffer for the maximum values provided by the maximum detector 30. Further, the system of FIG. 1 comprises an output element 50 which represents the maximum slew rate as stored by the buffer 40 at an electronic display. Preferably, the output element 50 comprises a numeric display which displays the current maximum slew rate. In another embodiment, the memory is combined with an averaging unit, the combination 40 receiving successive maximum values and forming the average of the received values. The resulting average is stored in the memory and retrieved by the output element 40 (or is supplied to the output element 50). According to a preferred embodiment, the combination 40 of the average and the memory forms the average of a fixed number of preceding average values. For example, the averager provides the mean value for the last twenty of fifty values supplied by the maximum detector 30. Further, the averager or the combination 40 of averager and memory can be adapted to form a sliding window average of the most recent N values, N being a positive integer. According to an alternative embodiment, the deviation unit 20 is a slew rate monitor which provides the slew rate (corresponding to the derivative) as a ratio between an increase and a respective distance of time spent by the increase. Thus, the deviation unit 20 forms a deviation of time discrete values.

The system of FIG. 2 can be provided by circuitry and/or by programmable hardware. In particular, some or all functions of the respective blocks can be provided as software modules. In this case, the connection between the individual blocks is provided by a module header or a function header comprising input and/or output variables. Preferably, block 10 comprises an analog/digital converter and/or following blocks. In particular blocks 20, 30 and 40 are provided by a microprocessor controlled by software.

Figure 2A:
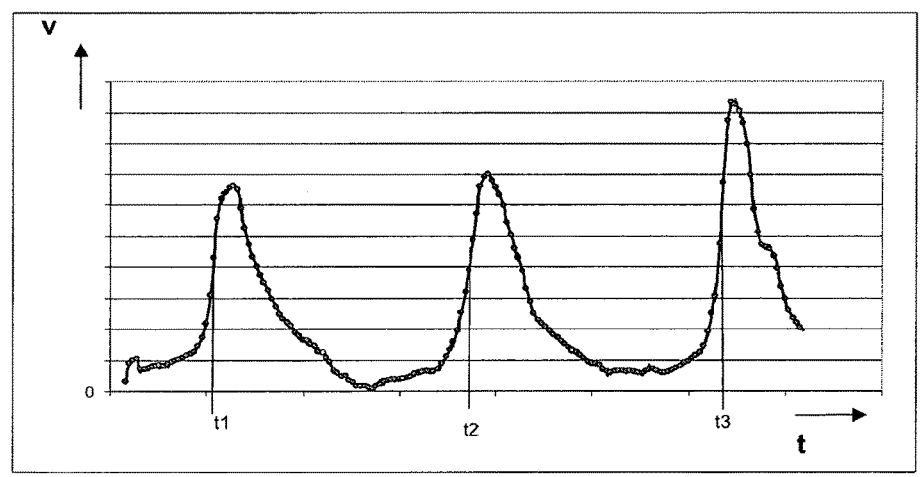
FIGS. 2A-2B show a typical temporal progression of blood flow velocity and a corresponding diagram of the first derivative of FIG. 2a with regard to time.

FIG. 2a shows the blood velocity in the course of time. In FIG. 2a, three heartbeats are shown in form of pulses each having a rising edge resulting from the systole. The progression of the blood flow condition (in this case the blood flow velocity) is represented by time discrete measuring points each measuring point shown as a dot. In addition, a line has been added connecting all dots in succession. As can be seen from FIG. 2a, the maximum slew rate of the first pulse is at t1, the maximum slew rate of the second pulse is at t2 and the maximum slew rate of the third pulse is at t3. These maximum increases represent the arteriovascular condition. In FIG. 2a, the blood velocity values are given as time discrete values reflecting individual measuring points. The time duration between two successive measuring points is equal for all successive points according to a sampling data acquisition procedure which periodically provides an measuring point according to the sampling rate of the data acquisition device, for example an analog/digital-converter, in particular a sample and hold unit thereof.

Figure 2B:
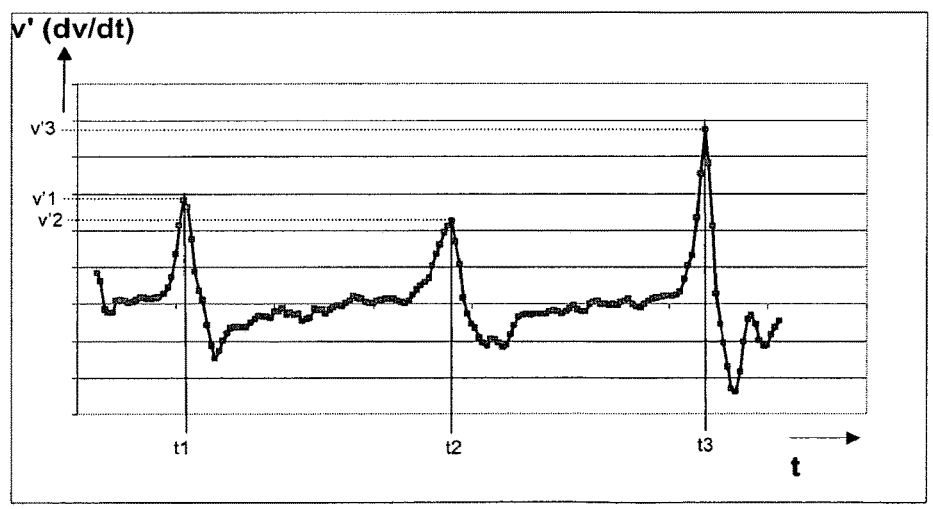

In FIG. 2b, the derivation with respect to time of the progression shown in FIG. 2a is given. The differentiation with respect to time is reflected by the symbol ' wherein v is a physical quantity (the velocity) and v' is equal to dv/dt. In a general aspect of the invention, dv/dt can be a differential quotient with $dt=t-t_0 \rightarrow 0$ or with $dt=t-t_0=\Delta t>0$. The points of time t1, t2 and t3 are identical to the points t1, t2 and t3 of FIG. 2a. At t1, the maximum slew rate is given as v'1, at t2, the maximum slew rate is v'2 and the maximum slew rate of the third pulse is given at v'3. According to the time discrete nature of the values shown in FIG. 2a, the derivation values in FIG. 2b are also time discrete and are represented as squares, together with a line connecting these squares. The derivation values shown in FIG. 2b are given as ratio between the increase shown in FIG. 2a (difference between two adjacent values) and the time distance between two successive points, that is the time interval corresponding to the sampling rate shown in FIG. 2a. The derivation at a point of time is equivalent to the difference between the physical quantity right before and right after the point of time divided by the time between both values (or multiplied by the sampling rate). Thus, a point reflecting the derivation always lies between the two data points or measuring points adjacent thereto.

FIGS. 3A-3F. In vivo measurements of red blood cell velocities in yolk sac arteries and veins.

(A) Overview of yolk sac vascular network in vivo. (B) Schematic representation of the vascular plexus. Arteries indicated in red, veins in blue. A1-A4 indicate the measurement sites in arteries, V1-V4 in veins. (C,D) red blood cell velocity profiles, and (E,F) the corresponding first order derivative of velocity—acceleration rate (dv/dt), in arteries and veins. Dotted line (C) indicates first order derivative for the time point of fastest acceleration (peak velocity increase, PVI). H, heart; VA, vitelline artery; VV, vitelline vein; SV, sinus vein. Scale bar, 3 mm in A.

FIGS. 4A-4F. Identification of flow signals that discriminate arteries from veins.

(A) time averaged mean red blood cell velocity increases with diameter in yolk sac arteries and veins. (B) mean shear rates are relatively constant for both arteries and veins. Regression line (solid lines) and 95% confidence interval (dotted lines) are indicated; regression coefficients are not significant. (C) red blood cell acceleration rate in arteries and veins. (D) acceleration rate as a function of mean velocity separates arterial from venous vessels. (E) acceleration rate normalized to mean velocity (relative pulse slope index—RPSI) as a function of diameter, yields separation of arterial (top) and venous (bottom) domain. Optimal separation of arterial from venous vessels occurs at a cutoff of RPSI=7.9 s$^{-1}$. (F) RPSI in arteries and veins. ***p<0.001; MannWhitney U-test.

Figure 5A:
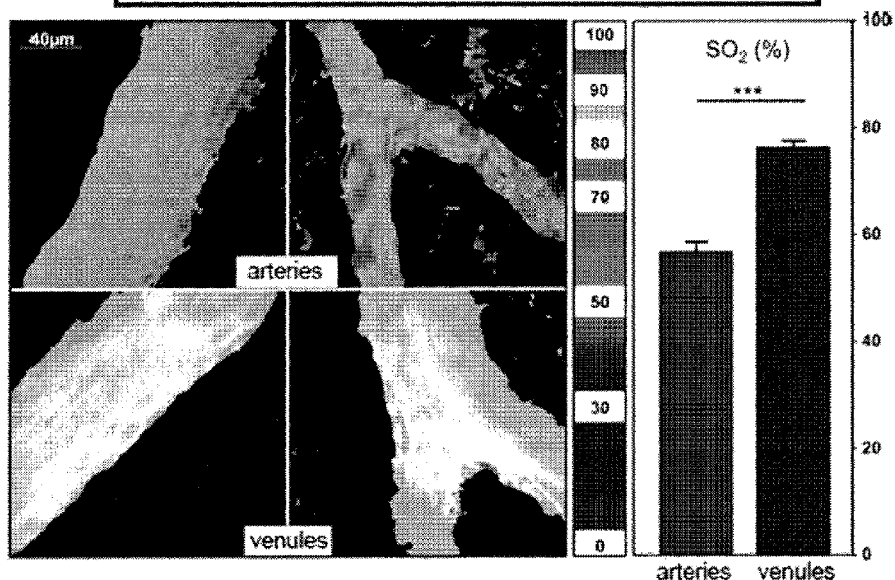
Figure 5B:
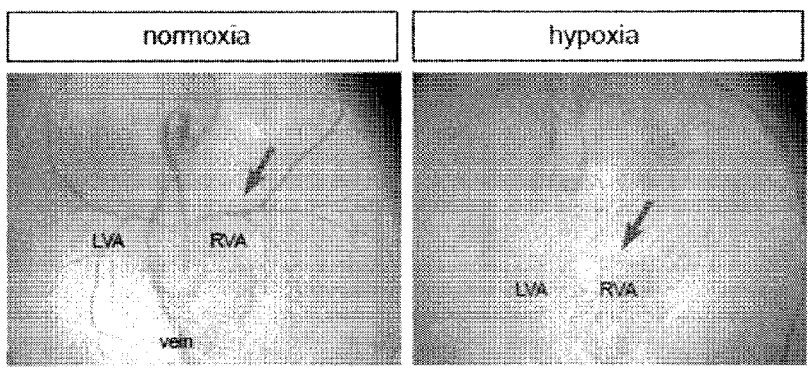

FIGS. 5A-5B. Role of oxygen in yolk sac remodeling.

(A) in vivo measurements of oxygen saturation shows significantly lower levels in arteries compared to veins. (B) exposing developing embryos to an ambient oxygen level of 10% O2 (hypoxia) impairs yolk sac arterial network growth (red arrow) compared to exposure to 21% O2 (normoxia). LVA, left vitelline artery; RVA, right vitelline artery.

FIGS. 6A-6F. Flow redistribution after right vitelline artery (RVA) ligation.

(A,B) Schematic representation of flow distribution in the yolk sac posterior pole, before (A) and after (B) ligation of the right vitelline artery (RVA). Note the reversal of flow direction in the RVA distal arterioles. In proximal and distal arterioles of the left vitelline artery (LVA), mean velocities (C,E) and mean shear rates (D,F) increased after RVA ligation, indicating that flow is shunted from the RVA to the LVA. *p<0.05, **p<0.01 pre-versus post ligation, Student's t-test. VV, vitelline vein; p, proximal arteriole; d, distal arteriole. Black arrows indicate normal flow direction, purple arrows the changed directions.

FIGS. 7A-7K. Flow redistribution results in formation of a collateral arterial network. Acutely after ligation FITC-dextran-angiography (A-D) indicates a perfusion deficit on ligated side (A). Asterisk indicates site of right vitelline artery ligation. Within 10 minutes post-ligation (B,C), blood starts to flow from the posterior venous domain towards the ligated side via pre-existing RVA arteriolar channels (D). Time-lapse imaging of this area (E-H) shows the rapid formation of an arterial network through the previously venous domain. At 24 h post ligation (I-K) a significant number of perfused large caliber arteries can be detected in ligation embryos, not in controls (K). Scale bars: 4.9 mm in A, 1.8 mm in B, 3.1 mm in C; 3.6 mm E-H; 2.4 mm in I.

FIGS. 8A-8H. Time lapse imaging of collateral arterial network formation after ligation (A-H) Still images from time-lapse movie show how the pre-existing RVA arteriolar segments at the ligated side (left part of image) enlarge, while the vitelline vein is progressively pruned. The pruning of the vein allows the LVA to expand through the former venous territory. With time, the thoroughfare channels obtaining the highest flow enlarge further and establish the collateral arterial network. Note the structural diameter increase of terminal arterioles of the LVA (red asterisk). Arrows indicate flow direction in vein (blue) and pre-existing arterioles (red). Flow direction in RVA is reversed in post compared to preligation. Yellow arrowhead indicates the pruned vitelline vein. LVA, left vitelline artery; RVA, right vitelline artery.

FIGS. 9A-9F. Adaptive lumen changes in the stem of the left and right vitelline artery after ligation. In vivo imaging of arterial diameter adaptation of right and left vitelline artery in control (A,C) and ligation (B,D) embryos shows progressive pruning of the right vitelline artery segment proximal to the ligation (F). The contralateral left vitelline artery in the ligation embryo now receives more flow and displays outward remodeling (E). LA, left vitelline artery; RA, right vitelline artery. *, p<0.05; ***p<0.001. Scale bars: Ø.62 mm in A,B; 1.25 mm in C,D.

Figure 10:
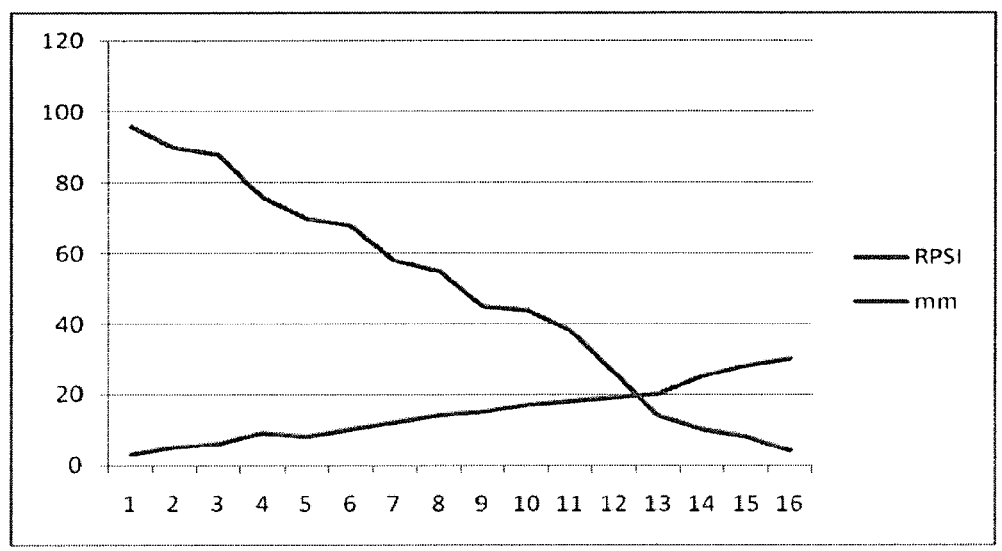

FIG. 10. Correlation between arterial diameter and RPSI in healthy patients.

The RPSI declines with increasing arterial diameter.

Figure 11:
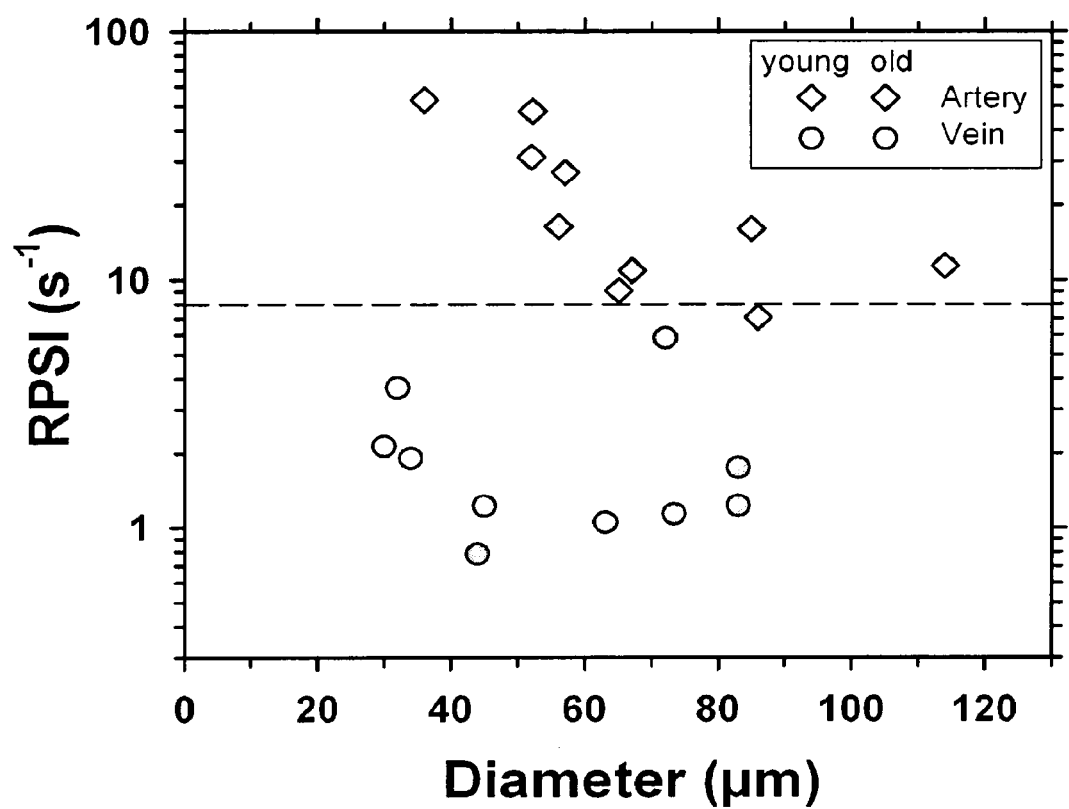

FIG. 11. Correlation between diameter and RPSI in young and old chicken embryos.

The RPSI declines with increasing arterial diameter.

Figure 12:
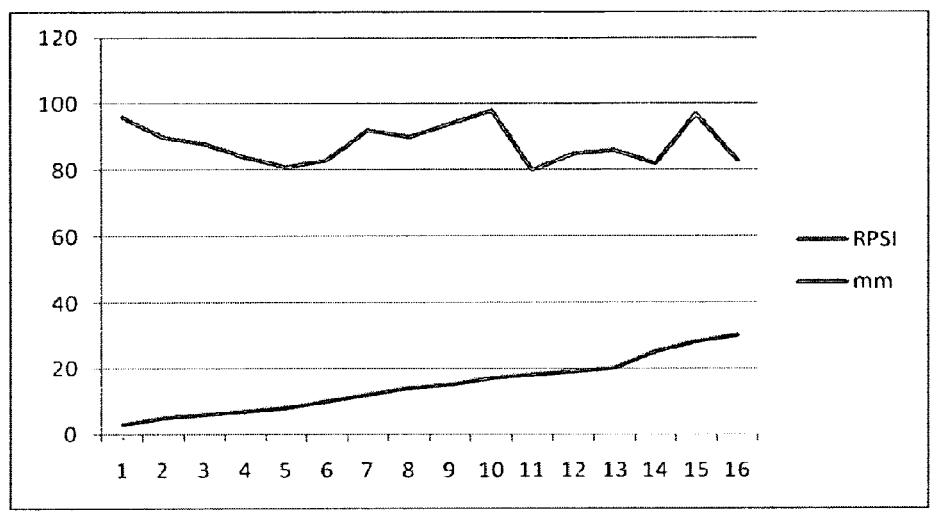

FIG. 12. Correlation between arterial diameter and RPSI in a shunt operated patient The RPSI remains constant in view of the increasing blood flow.

Figure 13:
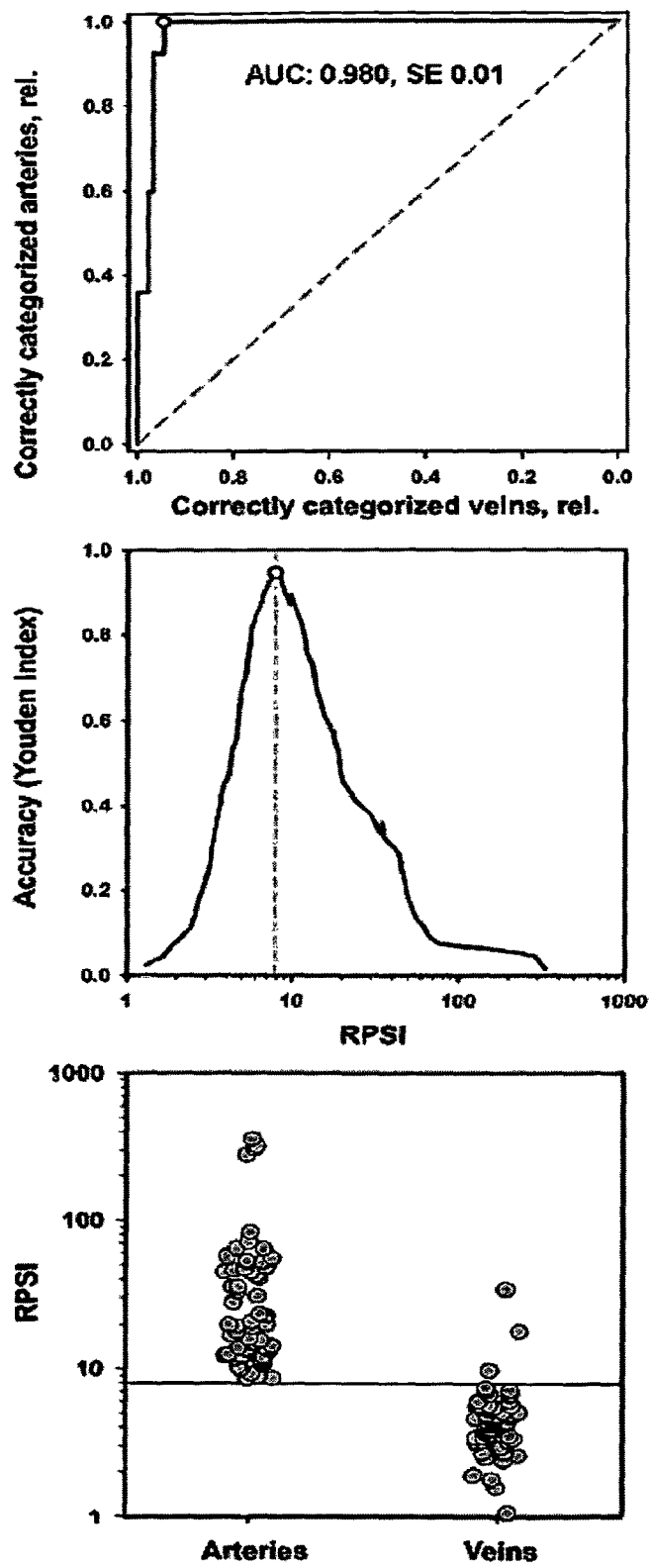

FIG. 13. Receiver Operator Characteristics Analysis.

Results of a Receiver Operator Characteristics (ROC) analysis, of the relative pulse slope index (RPSI), for the discrimination of arteries from veins. The top panel gives the ROC curve with an ROC area under the curve (AUC) of 0.98 (SE=0.01 1, p<0.0001). An AUC of 1 indicates a perfect separation while a random selection (corresponding to the diagonal dashed line shown in the graph) exhibits an AUC value of 0.5. The middle panel shows the dependence of accuracy of discrimination of arteries from veins from the chosen critical RPSI value. The accuracy of discrimination is calculated by the Youden index (J=max[SEi+SPi−1] where SEi and SPi are the sensitivity and specificity for a given RPSI values). The maximum accuracy value of J=0.8928 is achieved for an RPSI of 7.909 (circle) is marked by a circle in both panels. The discrimination of arteries and veins by this RPSI value (gray horizontal line, 7.9) is shown on the dot diagram in the lower panel. RPSI is given in s$^{-1}$.

EXAMPLE

1. Introduction

Arterial and venous vascular networks show a distinct genetic signature, function and branching architecture (De Smet et al., 2009; Swift and Weinstein, 2009). Specification of arterial-venous vessel identity and formation of branched vascular networks occur during early embryogenesis and are modulated by hemodynamic factors (Jones et al., 2004; le Noble et al., 2004; Lucitti et al., 2007), but the precise mechanisms are unclear. Circulation of blood creates mechanical forces in vessels (Garcia-Cardena et al., 2001; Jones et al., 2006), and affects oxygenation of developing organs. Here we investigated which mechanical forces, or secondary factors including oxygenation of the blood (Fraisl et al., 2009), might be relevant for regulating vessel identity in developing embryonic vascular networks in vivo. We furthermore assessed the morphological and genetic changes occurring in the embryonic yolk sac vasculature in response to manipulations of hemodynamic conditions, and show that genes strongly regulated herein, might also exert a functional role in collateral arterial network growth (Buschmann and Schaper, 1999; Schaper, 2009) during pathological conditions. In the embryo, vascular branching morphogenesis and vessel identity can be regulated by two distinct mechanisms: genetic hardwiring of vessel positioning and identity, and hemodynamics controlled vascular patterning and maintenance of vessel identity (Jones et al., 2006). Hardwiring of vessel positioning at the capillary level involves endothelial tip cells, and occurs independent of flow (Gerhardt et al., 2003; Hellstrom et al., 2007). Arterial specification requires activation of sonic hedgehog (shh)/VEGF/neuropilin-1/Notch pathways (Lawson et al., 2001; Lawson et al., 2002; Swift and Weinstein, 2009; Zhong et al., 2001). In the chick embryo manipulation of hemodynamic parameters changed the global patterning of arteries and veins in the yolk sac vasculature (le Noble et al., 2004).

In this example, we considered factors related to flow, pressure and oxygenation and performed a comprehensive in vivo analysis of these factors, substantiated by in vitro experiments. We found a unique parameter related to the pulsatility of blood flow, the relative pulse slope index (RPSI), which distinguishes arterial from venous domains.

2. Materials and Methods

Chick Embryos:

Fertilized chick (*Gallus gallus*, white leghorn) embryos were purchased from commercial sources and incubated at 38° C. in a humidified atmosphere. Embryo stages were determined according to the number of somites formed. Handling of the embryos and ligation of the right vitelline artery was performed as described previously (le Noble et al., 2004). FITC-Dextran (Sigma, Mw 200 kDa, 8 mg/ml in PBS) to visualize plasma flow was injected intravascular using a micropipette.

Flow Driven Models

The three vessels occlusion brain arteriogenesis (3-VO) model in male Sprague Dawley (SD) rats was performed as described (Busch et al., 2003; Buschmann et al., 2003). In short: both vertebral arteries were occluded via electrocoagulation. During the further occlusion of the left common carotid artery, cerebral blood flow was measured by laser Doppler flowmetry to ensure cerebral hypoperfusion. Three weeks after 3-VO, rats were anaesthetized and cerebral blood flow was measured via LDF after inducing maximal vasodilation with acetazolamide. To visualize the arteries of the circle of Willis colorized latex (Chicago Latex Products, no. 563) was perfused via a catheter into the maximally dilated (with Papaverin) cerebral arterial circulation. Vessel diameters were measured under the microscope.

The gap junction uncoupler carbenoxolone (Sigma) diluted in 0.9% NaCl was administered i.p. at a dosage of 1.184 mg/day (C57/Bl6 mice) or 1.48 mg/day (SD rats) for a period of 7 or 21 days respectively; controls received 0.9% NaCl. All animal experiments were approved by the local ethics committee.

In Vivo Microscopy: Time Lapse Imaging, Measurement of Red Blood Cell Velocity and Oxygen Saturation In vivo time-lapse imaging and intra vital video-microscopy were performed as described (le Noble et al., 2004; Lindert et al., 2002). In short: yolk sac blood vessels were imaged using a 25× objective (NA 0.6) and an asynchronous strobe light illumination (Lindert et al., 2002). This illumination generates image pairs with a time delay (delta t) of down to 0.5 ms. Using a spatial correlation approach, the spatial displacement (delta l) of the red cell column during this delay is determined off-line. The flow velocity is then calculated as V=delta l/delta t with a temporal resolution of 25 Hz for velocities up to 40 mm/s. For the determination of oxygen saturation, a multispectral approach was used (Styp-Rekowska et al., 2007).

Statistical Analysis

Data are expressed as the means±SEM. P values were calculated using Students t test or Mann Whitney U test (for non-normal distributions). A p value <0.05 was considered statistically significant.

3. Results 3.1 In Vivo Imaging of Blood Flow Parameters and Oxygen in Chick Embryo Arteries and Veins 3.1.1 Adaptation to Shear Stress, Identification of Relative Pulse Slope Index (RPSI) as a Parameter to Discriminate Arteries from Veins Red blood cell velocities (vRBC) were measured in arteries and veins in vivo (FIGS. 3a, 3b). We noted the striking pulsatility in the flow velocity profile in arteries (FIG. 3c) compared to the more constant flow velocity in veins (FIG. 3d). From the velocity profiles we calculated the red blood cell acceleration rate ($1^{st}$ order derivative, dv/dt, in $mm/s^2$, see red line in FIG. 3c) during each heart cycle. Note the steep acceleration rates during the initial systole in arteries (FIG. 3e), not in veins (FIG. 3f).

We next examined which flow related parameter discriminates arteries from veins (FIG. 4). In both arteries and veins, mean red blood cell velocity increased with increasing lumen diameter (FIG. 4a). The biological relevant parameter for vessel lumen adaptation to blood flow is the shear acting on the endothelial surface. Shear is proportional to the flow velocity with the proportionality factor depending inversely on the vessel diameter (mean velocity/vessel diameter). We estimated the time averaged (mean) shear rate as mean centerline flow velocity divided by vessel diameter (FIG. 4b). For arteries, (diameter range: 24-180 m; n=65 vessels; 10 animals) the typical mean shear rates ranged from 2 ($s^{-1}$) to 9 ($s_1$). Venous mean shear rates were slightly higher, averaging between 6-30 ($s^{-1}$) (n=60 vessels, 10 animals). These levels of shear rate are generally assumed to correlate to non-turbulent, laminar flow in microvessels. Regression line analysis (lines in FIG. 4b) revealed that the slope of the regression line was not significant for both arteries ($r^2$=0.035) and veins ($r^2$<0.006) (FIG. 4b). This indicates that both yolk sac arterioles and venules adapt their lumen diameter to maintain constant shear rates. Since shear rates of arteries and veins showed overlap, shear rate itself did not discriminate sufficiently between arteries and veins.

Figure 4A:
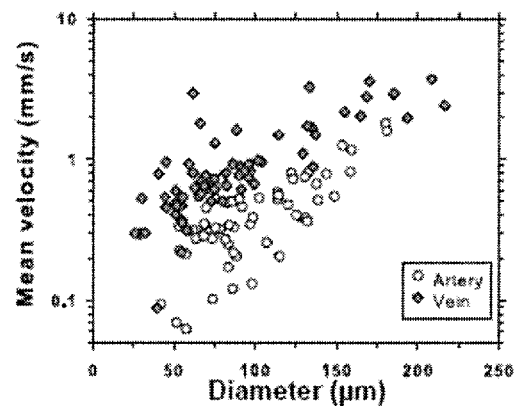
Figure 4B:
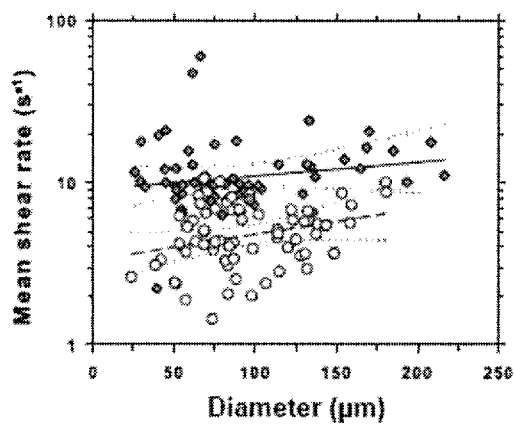
Figure 4C:
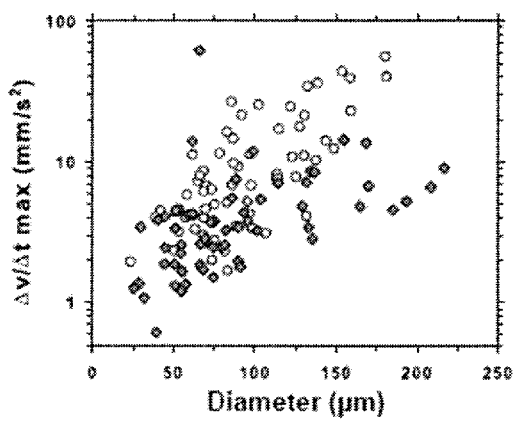

We next considered the acceleration rate (FIG. 4c). The peak velocity increase (PVI, dv/dt max) represents the maximal acceleration rate of the red blood cells, occurring in the early systole. The PVI increased with increasing diameter in both arteries and veins (FIG. 4c). In the smaller diameter range (<1 00 m) there was considerable overlap between acceleration rates obtained from the arterial or venous domain, and PVI too, did not discriminate sufficiently arteries from veins.

Figure 4D:
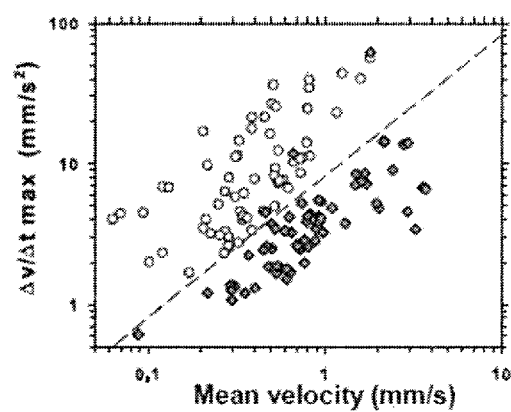

However, PVI in a vessel proved to vary systematically as a function of the mean velocity in that vessel (FIG. 4d). It was possible to achieve an almost complete separation of the arterial and venous domain by a line with slope 1 and a relation of PVI to mean velocity of 7.9 (see FIG. 13; Receiver Operator Analysis).

Figure 4E:
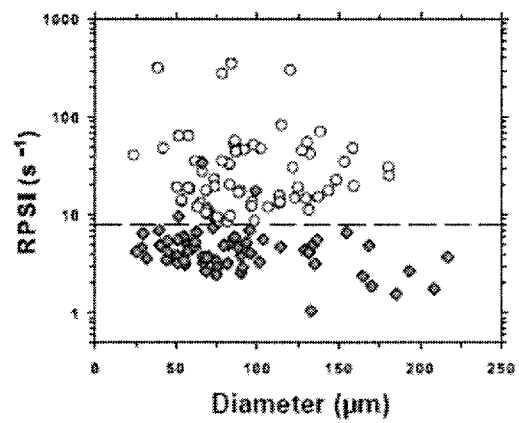
Figure 4F:
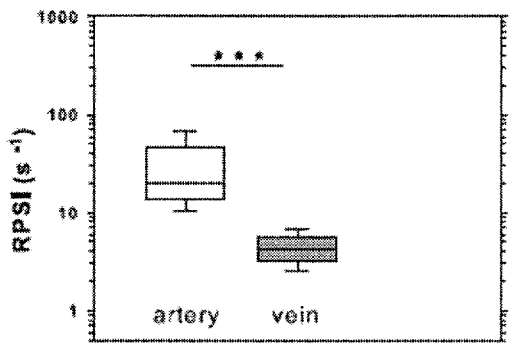

This observation suggests that the quotient PVI/mean velocity is suited to discriminate arteries from veins (FIG. 4e). The resulting parameter is referred to as relative pulse slope index (RPSI=PVI/mean vRBC in $s^{-1}$). RPSI was significantly higher in arteries compared to veins with almost no overlap between the two domains, at a cut-off value of 7.9 $s^{-1}$ (FIG. 4f, FIG. 13). Arteries have RPSI values exceeding 7.9 with 99% confidence.

3.1.2 Cyclic Stretch is Limited to the Aorta

In the adult, the distensible nature of the arteries averages out the pressure pulsations, allowing a continuous flow in the distal parts of arterial tree. We measured vessel distension (cyclic stretch) during the heart cycle in the dorsal aorta, and the yolk sac vitelline arteries and venules including the veins of the inflow tract. A small but significant amount of cyclic stretch (2.93%±0.57, n=23) was noted in aorta. In the vitelline arteries and venules, distension was not detectable in all animals investigated (n=1 5 animals, 5-6 arteries or veins per animal). The lack of distensibility supports pulsatile flow up to the distal parts of the yolk sac arterioles.

3.1.3 Oxygen Measurements in Arteries and Veins, Hypoxia Challenge In Vivo

The primary function of the yolk sac circulation is to take up nutrients from the yolk and allow gas ($O_2$, $CO_2$) exchange, equivalent to placenta function in mammals. In line with placenta function, we observed significantly lower ($p<0.001$) oxygen saturation levels in arteries (63.2%±1.9%) when compared to veins (78.4±3%, n=6; FIG. 5a). We next incubated chicken embryos in hypoxic conditions and examined arterial-venous network development (FIG. 5b). Exposure to an ambient oxygen level lower than 10% $O_2$ was embryonic lethal. Exposure to 10% $O_2$ induced growth retardation, cardiac malformations (in 7 out of 8 embryos), and bradycardia, when compared to age-matched normoxic (21% $O_2$) controls. In hypoxic embryos, the complexity of the arterial network—size of the vessels, and distal/lateral expansion of the network—was significantly reduced compared to normoxic controls (FIG. 5b). The adverse effects of hypoxia on embryonic cardiac function (Tintu et al., 2009), resulting in perfusion deficits may contribute to the impaired vascular development.

3.2 Flow Driven Macroscopic and Microscopic Changes in the Arterial Network

We next investigated how embryonic vessels adapt structure and branching pattern in response to changes in flow distribution using the chick embryo ligation model.

3.2.1 Increased Flow Velocities and Shear Rates in the Left Vitelline Arterial (LVA) Network after Ligation of the Right Vitelline Artery (RVA)

Figures 6A, 6B:
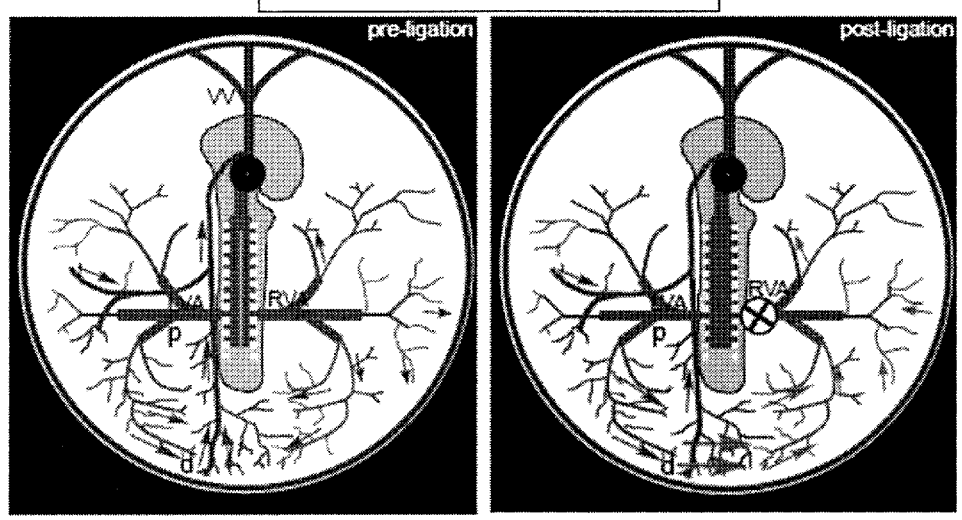
Figure 6C:
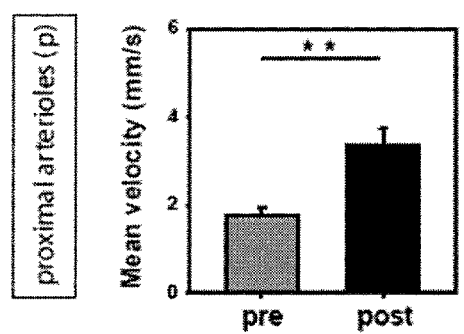
Figure 6D:
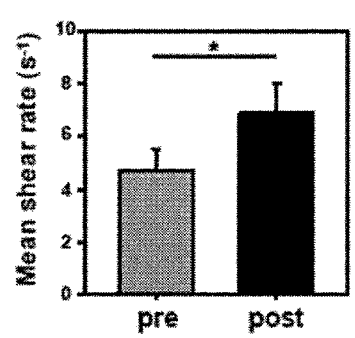
Figure 6E:
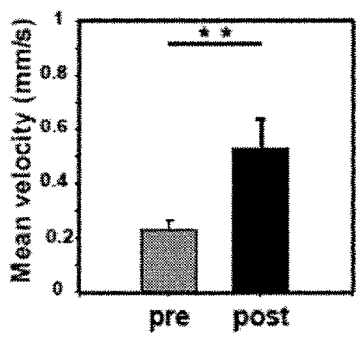
Figure 6F:
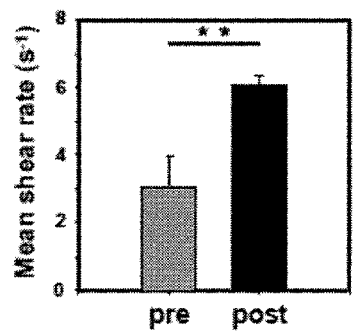

We first quantified the flow changes occurring in the proximal and distal parts of the left vitelline artery (LVA) after ligation of the right vitelline artery (RVA; FIGS. 6a,b; p indicates proximal, d—distal, measurements were made in the same vessel pre- and post ligation). In the LVA proximal arteries, mean velocities (FIG. 6c) increased significantly from 1.76±0.1 mm/s pre-ligation to 3.3±0.4 mm/s post ligation (n=12, $p<0.05$). We observed no acute diameter change in these arteries (% change pre-versus post-ligation was 1.02%, ns). Mean shear rates increased from 4.7±0.7 $s^{-1}$ pre-ligation to 6.9±1.1 $s^{-1}$ post-ligation (n=12, $p<0.05$; FIG. 6d). In the LVA distal arterioles mean velocities (FIG. 6e) significantly increased from 0.23±0.03 mm/s to 0.53±0.1 mm/s (n=12, $p<0.05$). Again, no acute diameter changes were observed. Also local application of acetylcholine (vasodilator) or norepinephrine (vasoconstrictor) did not affect diameter, indicating that these vessels have no acute regulation of vasomotor tone. The mean shear rates significantly increased from 3.3±0.6 $s^{-1}$ to 5.7±0.6 $s^{-1}$ (FIG. 6f). These data show that ligation of the RVA increased perfusion of the LVA arterial network up to the most distal branches.

3.2.2 Arterial Patterning Follows the Redistribution of Blood Flow

Redistribution of blood flow upon RVA ligation was evaluated using FITC-dextran angiography (FIGS. 7a-d). Acutely after ligation, the ligated right side showed a clear perfusion deficit; the LVA was well perfused (FIG. 7a). Within 10 minutes after ligation, some blood flow was recruited to the right side via retrograde perfusion of RVA arterioles in the posterior pole (FIGS. 7b,c). This blood flow was derived from the anterior venous plexus. Thus after ligation, blood flows from the LVA network, through the posterior vitelline vein domain, into the pre-existing arterioles of the RVA arterial network back to the heart (FIG. 7d). In these RVA arterioles the blood flow direction is reversed compared to pre-ligation, and pulsatility was reduced. RPSI values in ligated arterioles (n=5) dropped significantly from 11±0.5 (arterial domain) to 1±0.25 $s^{-1}$, thus showing venous flow characteristics. The reversal of flow direction in posterior pole was furthermore confirmed with intravital microscopy (supplemental movie 1 versus supplemental movie 2: note both changes in direction, and velocity). In the RVA pulsatility is lost after ligation because the blood flow used for perfusing it, comes from the LVA, and has to travel through the capillaries in the posterior pole that due their small diameter and high resistance dampen the pulsatile flow component.

Figure 7E:
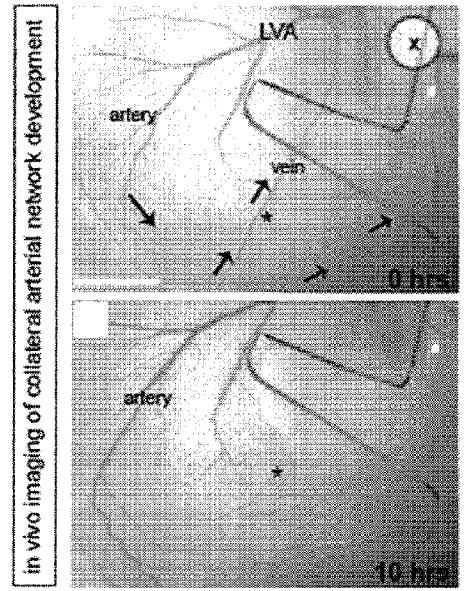
Figure 7F:
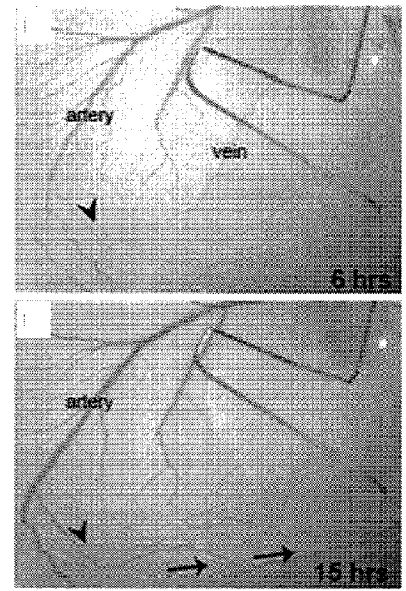
Figure 7G:
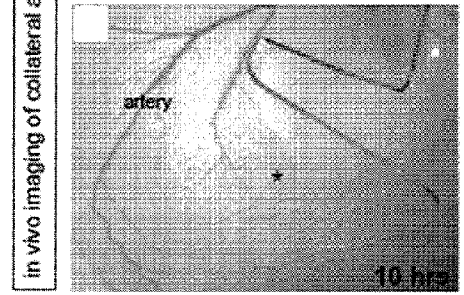
Figure 7H:
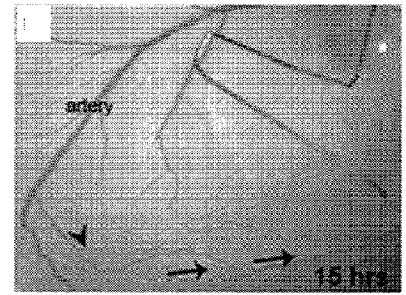
Figure 7I:
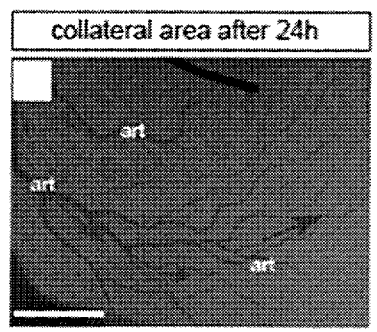
Figure 7J:
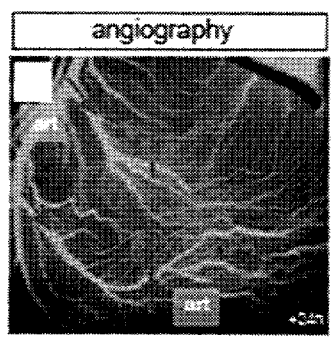
Figure 7K:
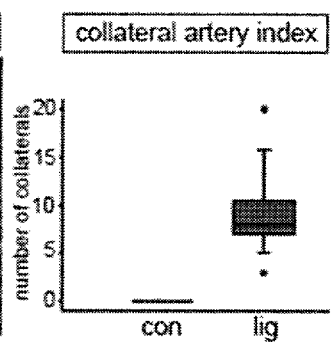
Figure 8A:
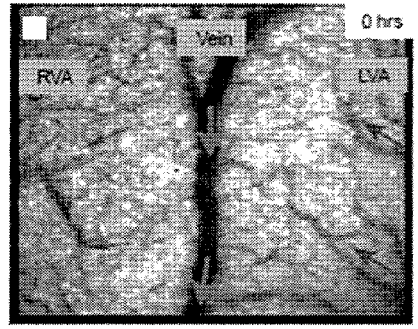
Figure 8B:
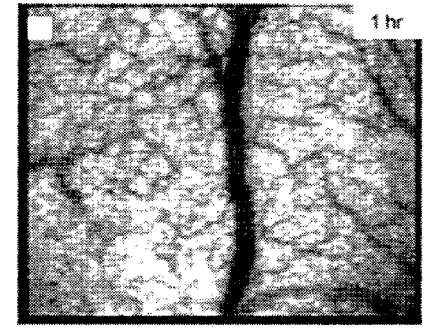
Figure 8C:
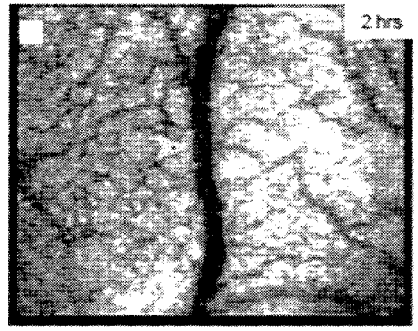
Figure 8D:
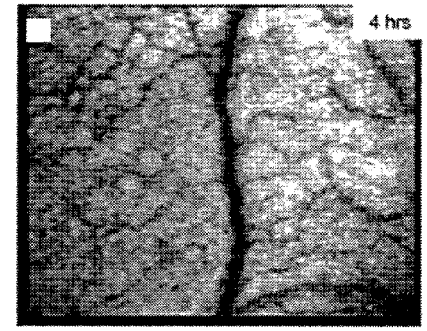
Figure 8E:
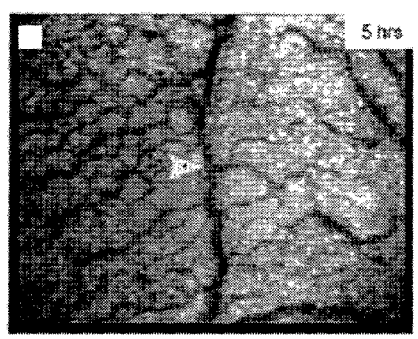
Figure 8F:
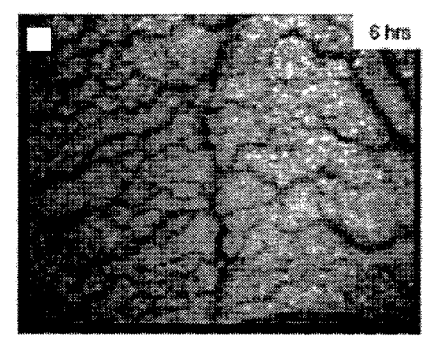
Figure 8G:
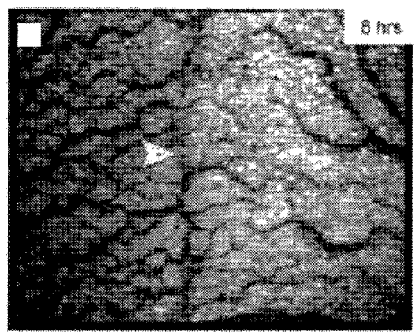
Figure 8H:
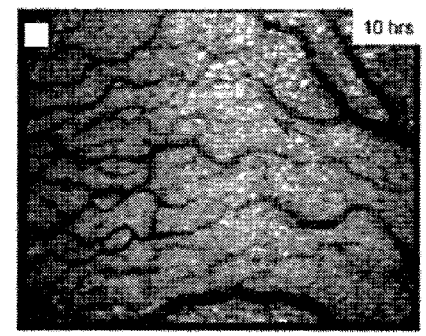
Figure 9A:
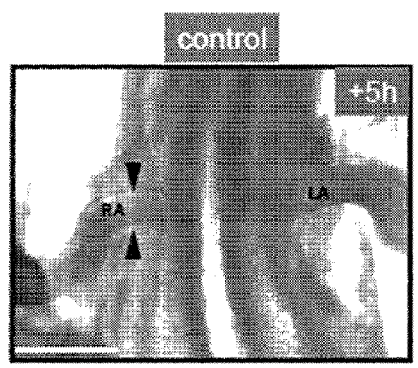
Figure 9B:
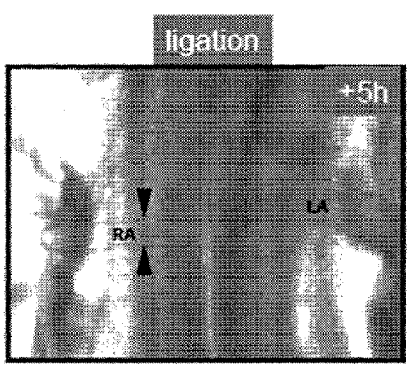
Figure 9C:
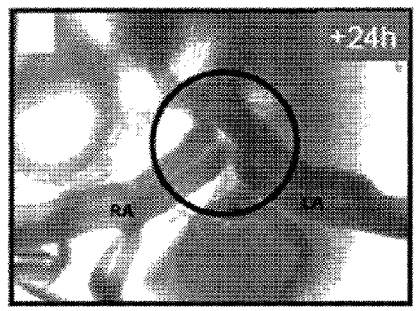
Figure 9D:
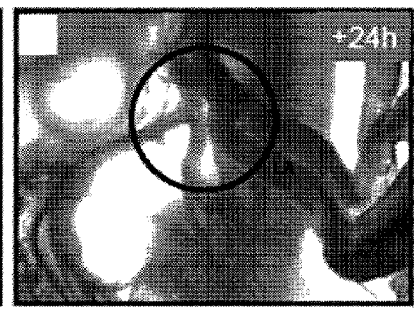
Figure 9E:
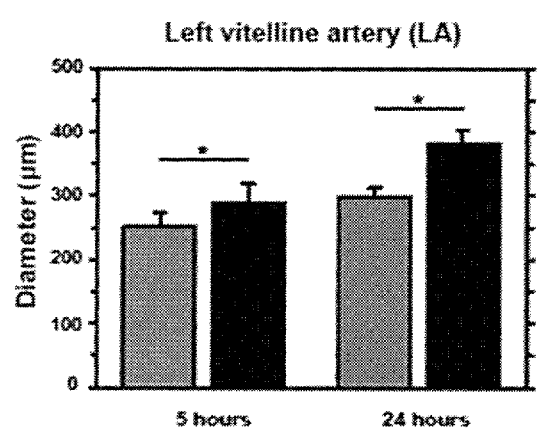
Figure 9F:
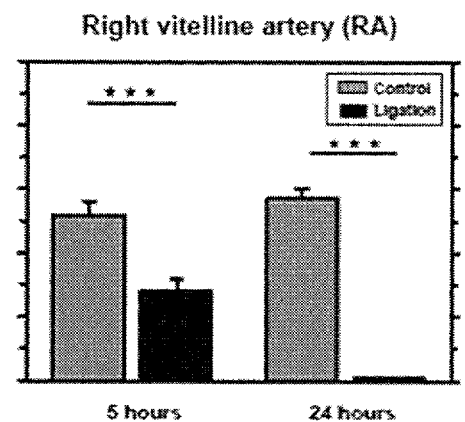

Within 15 hours, the changes in flow distribution, associated with a global change in arterial to patterning (FIGS. 7e-h). The LVA arterial network expanded towards the ligated right side with branches growing through the territory normally occupied by the veins, and projecting towards the right side of the embryo (FIGS. 7e-h). Concomitantly, the posterior vitelline vein regressed. At 24 hours post ligation, an elaborate collateral arterial network restoring flow to the occluded side was established in all embryos investigated (FIGS. 7i,j). Collateral arteries were defined by a clear anatomical connection to the LVA, carrying an arterial flow profile, and crossing the embryo/yolk sac midline (FIG. 7i,j). In ligated embryos the number of collateral arteries ranged from 3 to 20 (median=7, n=12 animals), in control embryos such collateral arteries were never observed in all animals (n=14) investigated (FIG. 7k).

We next imaged the microvascular changes in vivo using time-lapse intravital microscopy (supplemental movie 3, still images in FIG. 8). Acutely after ligation, blood flow coming from the terminal part of the LVA (FIG. 8a, red arrows) was distributed towards the vitelline veins (FIG. 8a, blue arrows) and the arterial network on the ligated side using pre-existing vessel segments (FIG. 8a, small red arrows, supplemental movie 3). The new flow direction (in supplemental movie 3, from the right side of the panel towards the left side) is perpendicular to the flow direction normally occurring in the venous territory. With time, the amount of flow attracted towards the ligated side increased, at the expense of flow entering the vein. The reduced flow toward the vein, associated with diameter reduction, and subsequent pruning of the vein (FIGS. 8a,c,e,g; yellow arrowhead). In contrast, the increased flow through the LVA distal arterioles and pre-existing segments on e ligated side induced a diameter increase in these vessels (FIG. 8, red asterisk).

3.2.3 Adaptive Arterial Diameter Remodeling after Right Vitelline Artery (RVA) Occlusion Ligation of the RVA resulted in pruning of the arterial segment proximal to the ligation and outward remodeling of the comparable arterial segment on the contralateral side (FIG. 9). At 5 hours post-ligation lumen diameters of the stem of the RVA were significantly smaller (ligation 140±20 tm versus 258±22 tm in time matched controls, $p<0.001$, n=6, FIGS. 9b,f) and after 24 hours, the right arterial segment was anatomically not detectable in all animals investigated (FIGS. 9d,f). In contrast, the arterial segment of the LVA showed increased diameters growth (FIGS. 9a-d) which was already detectable 5 hours post ligation (ligation 289±30 tm versus time matched control 252±22 tm; n=6 embryos, $p<0.05$, FIGS. 9a,e); and more pronounced after 24 hours (ligation 381±22 tm versus control 299±12 tm; n=6 embryos, $p<0.05$, FIGS. 9c,e). Thus, ligation of the RVA, results in shunting of flow to the LVA network causing outward remodeling in this area.

4. Discussion of the Example

Blood flow is needed to deliver oxygen to growing tissues in the embryo but also generates biomechanical forces including shear and wall stress (Jones et al., 2006). We performed an extensive in vivo analysis of artery-venous specific characteristics related to flow, pressure, and oxygen availability, and found that it is most likely that shear mediated signals contribute to regulation of arterial identity and remodeling.

We show that yolk sac arterioles and venules adapt their lumen size to the amount of flow carried as evidenced by maintenance of relatively constant shear rates, and rapid adjustment of lumen diameter in response to changes in flow. In artery occlusion experiments arteries exposed to increased flow, increase their diameter whereas pressurized arterial segments that don't carry flow regress. Ligation of the right vitelline artery induces the formation of a collateral arterial network branching from the contralateral left vitelline artery, transporting blood flow to the hypoperfused occluded side. This collateralization process involves flow driven "upgrading" of capillary segments into arterioles guided by the flow gradient. Within 24 hours it results in complete restoration of blood flow to the ligated area. Since acute vasomotor responses were not observed, the diameter changes occurring post ligation, are of structural nature. Anatomical properties of yolk sac arterioles including an incomplete vessel wall may facilitate this rapid structural adaptation.

We noted striking differences in flow pulsatility between arteries and veins in vivo. Theoretically, the steepness of the shear increase during the early systole would be the strongest pulsatile signal available to endothelial cells. The best separation between arterial and venous vessels was indeed obtained by estimating this signal, i.e. the maximal positive change in shear rate relative to the time averaged shear rate in the same vessel called relative pulse slope index, RPSI $[s^{-1}]$. Arteries have RPSI values exceeding 7.9 with 99% confidence, while the respective probability is only 5% for veins. Of course these observations don't prove causality and for RPSI to be physiologically relevant, endothelial cells have to sense fluctuations in shear (Dai et al., 2004; Garcia-Cardena et al., 2001). We show in vitro that arterial endothelial cells exposed to pulsatile shear maintain expression of the arterial marker ephrinB2, which was not observed with constant shear. In vivo, RPSI above 7.9 correlated well with arterial marker expression. Right vitelline artery (RVA) ligation, caused RPSI in perfused vessels on the ligated side to drop from the arterial (above 7.9) to venous domain (below 7.9) This suggests that in this setting, pulsatile flow/shear, not pressure, regulates arterial identity genes.

Although our observations offer some explanation for arterial-venous fate control by flow, relevant questions remain. Previous studies showed that during early embryogenesis both arterial and venous endothelial cells can change their genetic identity, in response to alterations in local cues (le Noble et al., 2004; Moyon et al., 2001). However, with time this plasticity is lost, through a yet unknown mechanism (Moyon et al., 2001). Adult veins exposed to arterial flow regimes loose venous identity genes, but don't acquire arterial markers (Kudo et al., 2007). Our failure to induce an arterial phenotype in venous cells in vitro may also reflect this loss of plasticity. The vessels we studied are rather immature in both function and structure. In adult vessels, with an intact mature vessel wall, remodeling may require more time or additional digestive actions. It is therefore clear that our observations can't be generalized for all conditions in the adult, and contribution of signals from perivascular nerves has to be considered (Larrivee et al., 2009). In the chick embryo yolk sac, arterial pressures are extremely low and range from 0.4 mmHg (stage14) to about 1.35-0.8 mmHg (stage 23) (Girard, 1973; Van Mierop, 1970; Van Mierop and Bertuch, 1967). Venous pressures were lower than 0.2 mmHg. If absolute pressure values discriminate arteries from veins, endothelial cells should be capable of sensing a threshold pressure around 0.4 mmHg. To our knowledge thus far no evidence showing such a value in the context of arterial-venous differentiation in endothelial cells exists. Instead, some studies show that, in the adult arterial marker expression might be modulated via pressure related cyclic stretch of the vessel wall (Korff et al., 2008). Our in vivo observations indicate that, if any, the contribution of cyclic stretch in determining expression of identity genes is limited to embryonic aorta and outflow tract.

REFERENCES FOR THE EXAMPLE

Busch, H. J., Buschmann, I. R., Mies, G., Bode, C. and Hossmann, K. A. (2003). Arteriogenesis in hypoperfused rat brain. *J Cereb Blood Flow Metab* 23, 62 1-8.

Buschmann, I. and Schaper, W. (1999). Arteriogenesis Versus Angiogenesis: Two Mechanisms of Vessel Growth. *News Physiol Sci* 14, 121-125.

Buschmann, I. R., Busch, H. J., Mies, G. and Hossmann, K. A. (2003). Therapeutic induction of arteriogenesis in hypoperfused rat brain via granulocyte-macrophage colony-stimulating factor. *Circulation* 108, 610-5.

Dai, G., Kaazempur-Mofrad, M. R., Natarajan, S., Zhang, Y., Vaughn, S., Blackman, B. De Smet, F., Segura, I., De Bock, K., Hohensinner, P. J. and Carmeliet, P. (2009). Mechanisms of vessel branching: filopodia on endothelial tip cells lead the way. *Arterioscler Thromb Vasc Biol* 29, 63 9-49.

Fraisl, P., Mazzone, M., Schmidt, T. and Carmeliet, P. (2009). Regulation of angiogenesis by oxygen and metabolism. *Dev Cell* 16, 167-79.

Garcia-Cardena, G., Comander, J., Anderson, K. R., Blackman, B. R. and Gimbrone, M. A., Jr. (2001). Biomechanical activation of vascular endothelium as a determinant of its functional phenotype. *Proc Natl Acad Sci USA* 98, 4478-85.

Gerhardt, H., Golding, M., Fruttiger, M., Ruhrberg, C., Lundkvist, A., Abramsson, A., Girard, H. (1973). Arterial pressure in the chick embryo. *Am J Physiol* 224, 454-60.

Hellstrom, M., Phng, L. K., Hofmann, J. J., Wallgard, E., Coultas, L., Lindblom, P., Jones, E. A., Baron, M. H., Fraser, S. E. and Dickinson, M. E. (2004). Measuring hemodynamic changes during mammalian development. *Am J Physiol Heart Circ Physiol* 287, H1561-9.

Jones, E. A., le Noble, F. and Eichmann, A. (2006). What determines blood vessel structure? Genetic prespecification vs. hemodynamics. *Physiology (Bethesda)* 21, 388-95.

Korff, T., Braun, J., Pfaff, D., Augustin, H. G. and Hecker, M. (2008). Role of ephrinB2 expression in endothelial cells during arteriogenesis: impact on smooth muscle cell migration and monocyte recruitment. *Blood* 112, 73-81.

Kudo, F. A., Muto, A., Maloney, S. P., Pimiento, J. M., Bergaya, S., Fitzgerald, T. N., Westvik, T. S., Frattini, J. C., Breuer, C. K., Cha, C. H. et al. (2007). Venous identity is lost but arterial identity is not gained during vein graft adaptation. *Arterioscler Thromb Vasc Biol* 27, 1562-71.

Larrivee, B., Freitas, C., Suchting, S., Brunet, I. and Eichmann, A. (2009). Guidance of vascular development: lessons from the nervous system. *Circ Res* 104, 428-41.

Lawson, N. D., Scheer, N., Pham, V. N., Kim, C. H., Chitnis, A. B., Campos-Ortega, J. A. and Weinstein, B. M. (2001).

Notch signaling is required for arterial-venous differentiation during embryonic vascular development. *Development* 128, 3675-83.

Lawson, N. D., Vogel, A. M. and Weinstein, B. M. (2002). sonic hedgehog and vascular endothelial growth factor act upstream of the Notch pathway during arterial endothelial differentiation. *Dev Cell* 3, 127-36.

le Noble, F., Moyon, D., Pardanaud, L., Yuan, L., Djonov, V., Matthijsen, R., Breant, C., Fleury, V. and Eichmann, A. (2004). Flow regulates arterial-venous differentiation in the chick embryo yolk sac. *Development* 131, 361-75.

Lindert, J., Werner, J., Redlin, M., Kuppe, H., Habazettl, H. and Pries, A. R. (2002). OPS imaging of human microcirculation: a short technical report. *J Vasc Res* 39, 368-72.

Lucitti, J. L., Jones, E. A., Huang, C., Chen, J., Fraser, S. E. and Dickinson, M. E. (2007). Vascular remodeling of the mouse yolk sac requires hemodynamic force. *Development* 134, 33 17-26.

Moyon, D., Pardanaud, L., Yuan, L., Breant, C. and Eichmann, A. (2001). Plasticity of endothelial cells during arterial-venous differentiation in the avian embryo. *Development* 128, 3359-70.

Schaper, W. (2009). Collateral circulation: past and present. *Basic Res Cardiol* 104, 5-21.

Styp-Rekowska, B., Disassa, N. M., Reglin, B., Ulm, L., Kuppe, H., Secomb, T. W. and Pries, A. R. (2007). An imaging spectroscopy approach for measurement of oxygen saturation and hematocrit during intravital microscopy. *Microcirculation* 14, 207-21.

Swift, M. R. and Weinstein, B. M. (2009). Arterial-venous specification during development. *Circ Res* 104, 576-88.

Tintu, A., Rouwet, E., Verlohren, S., Brinkmann, J., Ahmad, S., Crispi, F., van Bilsen, M., Carmeliet, P., Staff, A. C., Tjwa, M. et al. (2009). Hypoxia induces dilated cardiomyopathy in the chick embryo: mechanism, intervention, and long-term consequences. *PLoS One* 4, e5155.

Van Mierop, L. H. (1970). Blood pressure in chick embryos. *UCLA Forum Med Sci* 10, 27-36.

Van Mierop, L. H. and Bertuch, C. J., Jr. (1967). Development of arterial blood pressure in the chick embryo. *Am J Physiol* 212, 43-8.

Zhong, T. P., Childs, S., Leu, J. P. and Fishman, M. C. (2001). Gridlock signalling pathway fashions the first embryonic artery. *Nature* 414, 216-20.

The invention claimed is:

1. A method for determining a measure of an arteriogenic capacity of a subject having an arterial blood flow, comprising:

determining a temporal progression of an instantaneous blood flow condition of the arterial blood flow;

deriving a slew rate of the temporal progression during an increase of the temporal progression;

determining the maximum of the slew rate (peak velocity increase (PVI));

determining red blood cell velocities in the arterial blood flow (vRBC); and determining a relative pulse slope index (RPSI) by forming the quotient of the PVI and a mean of the vRBC in the arterial blood flow, wherein the measure of arteriogenic capacity is a monotone function determined by the RPSI, outputting the measure of the arteriogenic capacity to an output element of an indicator device, thereby providing an indication of the arteriogenic capacity of the subject, and activating an actuator element that applies an external pressure to the subject in response to the output of the measure of the arteriogenic capacity.

2. The method of claim 1, wherein determining the temporal progression of the instantaneous blood flow condition comprises a step of measuring at least one of the following physical quantities: an instantaneous blood flowvelocity, an instantaneous fluid pressure or an instantaneous shearing force within an arteriovascular section of the subject, the method further comprising a step of determining the blood flow condition according to a predefined function of at least one of the physical quantities.

3. The method of claim 2, wherein the value representing the maximum of the slew rate corresponds to (a) the maximum slew rate of the instantaneous blood flow velocity, (b) the maximum slew rate of the instantaneous fluid pressure, or (c) the maximum slew rate of the instantaneous shearing force, or (d) one of these maximum slew rates normalized by a mean value of the blood flow velocity, of the fluid pressure or of the shearing force or (e) one of these slew rates normalized by the ratio of the mean value of the blood flow velocity, of the fluid pressure or of the shearing force to the cross sectional diameter of the arteriovascular section or to a fraction thereof.

4. The method of claim 1, wherein deriving the slew rate of the temporal progression comprises: determining the slew rate by deriving the progression of the blood flow condition with respect to time; or determining the slew rate by relating an increase of the progression to the distance of time spanned by the increase.

5. The method of claim 1, wherein the temporal progression is represented by a time-discrete blood flow condition signal comprising at least two values of the same positive slope or by a time-continuous blood flow condition signal comprising at least one positive slope.

6. The method of claim 1, comprising repeatedly determining a variation of an arteriovascular condition with a repetition in time intervals greater than 5 days, wherein the variation of the arteriovascular condition is in monotone increasing relationship to a measure for an arteriogenic capacity of the subject reflecting the progress of an arteriovascular condition of the subject or reflecting a response on physical training of the subject; wherein the measure for the arteriogenic capacity is determined according to the variation and the relationship.

7. The method of claim 1, wherein the vascular condition is determined by a plurality of consecutive individual arteriovascular condition determinations and by averaging the resulting individual arteriovascular conditions, or by identifying the maximum of the resulting individual arteriovascular conditions.

8. The method of claim 1, wherein determining a temporal progression of a blood pressure quantity comprises measuring blood flow properties within an arteriovascular section of the subject by laser Doppler velocimetry, sonography or magnetic resonance imaging of the arteriovascular section, or by pressure sensing according to wrist blood pressure monitoring, finger blood pressure monitoring, sphygmomanometry, plethysmometry, plethysmography, or intravascular blood pressure sensing, or impedance measurements of tissue or at the arteriovascular section or at a myocardial section.

* * * * *